US008440406B2

(12) United States Patent
Johnson et al.

(10) Patent No.: US 8,440,406 B2
(45) Date of Patent: May 14, 2013

(54) AMPLIFICATION PRIMERS WITH NON-STANDARD BASES FOR INCREASED REACTION SPECIFICITY

(75) Inventors: Scott Johnson, Sun Praire, WI (US); Kathleen Engelbrecht, Madison, WI (US); Tiruvidaimarudur S. Ramasubramanian, Mequon, WI (US)

(73) Assignee: Luminex Corporation, Austin, TX (US)

( * ) Notice: Subject to any disclaimer, the term of this patent is extended or adjusted under 35 U.S.C. 154(b) by 51 days.

(21) Appl. No.: 12/910,113

(22) Filed: Oct. 22, 2010

(65) Prior Publication Data

US 2011/0097764 A1 Apr. 28, 2011

Related U.S. Application Data

(60) Provisional application No. 61/254,281, filed on Oct. 23, 2009.

(51) Int. Cl.
*C12Q 1/68* (2006.01)
*C12P 19/34* (2006.01)

(52) U.S. Cl.
USPC .................... 435/6.12; 435/6.1; 435/6.11

(58) Field of Classification Search ........................ None
See application file for complete search history.

(56) References Cited

U.S. PATENT DOCUMENTS

| | | | |
|---|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,996,143 A | 2/1991 | Heller et al. |
| 5,210,015 A | 5/1993 | Gelfand et al. |
| 5,432,272 A | 7/1995 | Benner |
| 5,604,097 A | 2/1997 | Brenner |
| 5,605,794 A | 2/1997 | Rust et al. |
| 5,679,524 A | 10/1997 | Nikiforov et al. |
| 5,681,702 A | 10/1997 | Collins et al. |
| 5,736,330 A | 4/1998 | Fulton |
| 5,780,233 A | 7/1998 | Guo et al. |
| 5,843,669 A | 12/1998 | Kaiser et al. |
| 5,846,717 A | 12/1998 | Brow et al. |
| 5,856,092 A | 1/1999 | Dale et al. |
| 5,866,336 A | 2/1999 | Nazarenko et al. |
| 5,912,147 A * | 6/1999 | Stoler et al. ................. 435/91.2 |
| 5,928,869 A | 7/1999 | Nadeau et al. |
| 5,965,364 A | 10/1999 | Benner |
| 6,001,983 A | 12/1999 | Benner |
| 6,007,984 A | 12/1999 | Wang et al. |
| 6,037,120 A | 3/2000 | Benner |
| 6,046,807 A | 4/2000 | Chandler |
| 6,057,107 A | 5/2000 | Fulton |
| 6,077,668 A | 6/2000 | Kool |
| 6,140,496 A | 10/2000 | Benner |
| 6,232,462 B1 | 5/2001 | Collins et al. |
| 6,287,766 B1 | 9/2001 | Nolan et al. |
| 6,294,336 B1 | 9/2001 | Boyce-Jacino et al. |
| 6,511,809 B2 | 1/2003 | Baez et al. |
| 6,548,250 B1 | 4/2003 | Sorge |
| 6,833,257 B2 | 12/2004 | Lee et al. |
| 6,977,161 B2 | 12/2005 | Grenier et al. |
| 7,422,850 B2 | 9/2008 | Marshall et al. |
| 7,517,651 B2 | 4/2009 | Marshall et al. |
| 7,541,147 B2 | 6/2009 | Marshall et al. |
| 7,579,154 B2 | 8/2009 | Chun |
| 2002/0132221 A1 | 9/2002 | Chee et al. |
| 2002/0150900 A1 | 10/2002 | Marshall et al. |
| 2003/0194705 A1 | 10/2003 | Schroth |
| 2006/0252091 A1 | 11/2006 | Marshall et al. |
| 2007/0172824 A1 | 7/2007 | Chun |
| 2007/0264694 A1 | 11/2007 | Prudent |
| 2009/0226926 A1 | 9/2009 | Marshall et al. |
| 2010/0291570 A1 | 11/2010 | Marshall et al. |
| 2011/0124053 A1* | 5/2011 | Benner et al. ................. 435/91.2 |
| 2011/0257046 A1* | 10/2011 | Schroeder ........................ 506/32 |

FOREIGN PATENT DOCUMENTS

| | | |
|---|---|---|
| CA | 2409309 | 11/2001 |
| EP | 0 382 433 | 8/1990 |
| EP | 0 416 815 | 3/1991 |
| EP | 0 416 817 | 3/1991 |
| EP | 0 742 287 | 11/1996 |
| EP | 0 915 174 | 5/1999 |
| EP | 1 349 954 | 10/2003 |
| EP | 1400601 | 3/2004 |
| WO | WO-90/06042 | 6/1990 |
| WO | WO-94/21820 | 9/1994 |
| WO | WO-96/31622 | 10/1996 |
| WO | WO-97/46711 | 11/1997 |
| WO | WO-98/14610 | 4/1998 |
| WO | WO-01/90417 | 11/2001 |

OTHER PUBLICATIONS

Barnes WM., "The fidelity of Taq polymerase catalyzing PCR is improved by an N-terminal deletion," Gene, 112(1):29-35 (1992).
Beaucage et al., "Deoxynucleoside phosphoramidites—a new class of key intermediates for deoxypolynucleotide synthesis," 1981, Tetrahedron Letters 22(20):1859-1862.

(Continued)

*Primary Examiner* — Young J Kim
(74) *Attorney, Agent, or Firm* — Fulbright & Jaworski L.L.P.

(57) ABSTRACT

Described herein are methods for increasing the annealing specificity of an amplification reaction using Iso-base Amplification Primers ("IAPs"). IAPs containing an iso-region are capable of regulating sequence-specific annealing thereby enhancing primer-template hybridization for sequence-specific amplification of nucleotides.

12 Claims, 1 Drawing Sheet

OTHER PUBLICATIONS

Borer et al., "Stability of Ribonucleic acid and double-stranded helices," J. Mol. Biol., 86:843-853, 1974.

Brown et al., "Chemical synthesis and cloning of a tyrosine tRNA gene," (1979) Methods in Enzymology 68:109-151.

Bult et al., "Complete genome sequence of the Methanogenic Archaeon, *Methanococcus jannaschii*," Science, 273:16 pages, 1996.

Cantor, "Lighting up Hybridization," Nature Biotechnology, 14(1):264, 1996.

Chou et al., "Solid-phase synthesis and high-resolution NMR studies of two synthetic double-helical RNA dodecamers: r(CGCGAAUUCGCG) and r(CGCGUAUACGCG)," Biochemistry, 28: 2422-2435, 1989.

Cobianchi et al., "Enzymes for Modifying and Labeling DNA and RNA", Methods in Enzymology, Academic Press, Inc., 152: 94-110, 1987.

Dong et al., "Flexible use of high-density oligonucleotide arrays for single-nucleotide polymorphism discovery and validation," Genome Research, 11:1418-1424, 2001.

Guatelli et al., "Isothermal, in vitro amplification of nucleic acids by a multienzyme reaction modeled after retroviral replication," Proc. Natl Acad. Sci., 87(5):1874-1878, Mar. 1990.

Hacia et al., "Detection of heterozygous mutations in BRCA1 using high density oligonucleotide arrays and two-colour fluorescence analysis," Nature Genetics, 14:441-447, Dec. 1996.

Hosfield et al., "Newly discovered archaebacterial flap endonucleases show a structure-specific mechanism for DNA substrate binding and catalysis resembling human flap endonuclease-1," J. Biol. Chem., 273(42):27154-27161, Issue of Oct. 16, 1998.

International Search Report and Written Opinion received for PCT/US2010/053773 dated Jan. 17, 2011.

Jain, K.K., "Applications of biochip and microarray systems in pharmacogenomics," Pharmacogenomics, 289-307, 2000.

Jurczyk et al., "Synthesis of 2'-Deoxyisoguanosine 5'-Triphosphate and 2'-Deoxy-5-methylisocytosine 5'-Triphosphate," Helvetica Chimica Acta, 82: 1005-1015 (1999).

Kälin et al., "Evaluation of the ligase chain reaction (LCR) for the detection of point mutations," Mutat. Res., 283:119-123, 1992.

La Rocco et al., "Evaluation of a commercial rRNA amplification assay for direct detection of mycobacterium tuberculosis in processed sputum," Eur. J. Clin. Microbiol. Infect. Dis., 13(9):726-731, Sep. 1994.

Livak et al., "Oligonucleotides with Fluorescent Dyes at Opposite Ends Provide a Quenched Probe System Useful for Detecting PCR Product and Nucleic Acid Hybridization," PCR Methods and Applications, 4(6):357-362, 1995.

Lizardi et al., "Mutation detection and single-molecule counting using isothermal rolling-circle amplification," Nat. Genet., 19:225-232, Jul. 1998.

Lyamichev et al., "Structure-specific endonucleolytic cleavage of nucleic acids by eubacterial DNA polymerases," Science, 260(5109):778-83 May 7, 1993.

McMinn et al., "Efforts toward Expansion of the Genetic Alphabet: DNA Polymerase Recognition of a Highly Stable, Self-Pairing Hydrophobic Base," J. Am. Chem. Soc. 121(49):11585-11586 Dec. 15, 1999.

Morrison, Detection of Energy Transfer and Florescence Quenching in Nonisotopic Probing, Blotting and Sequencing, Academic Press, Inc., Second Edition, 429-471 (1995).

Moser et al., "Exploiting the Enzymatic Recognition of an Unnatural Base Pair to Develop a Universal Genetic Analysis System," Clinical Chemistry, 49(3), 407-414 (2003).

Narang et al., "Improved phosphotriester method for the synthesis of gene fragments," Methods in Enzymology, Academic Press, Inc., 68:90-98, (1979).

Newton et al., "The production of PCR products with 5' single-stranded tails using primers that incorporate novel phosphoramidite intermediates," Nucleic Acids Research, 21(5):1155-1162 (1993).

Nolan et al., "SNP Scoring for Drug Discovery Applications," Integrated Technologies for Drug Discovery, Chap. 6, SNP Scoring, 1-15 (2002).

Ogawa et al., "Efforts toward the Expansion of the Genetic Alphabet: Information Storage and Replication with Unnatural Hyrdrophobic Base Pairs," J. Am. Chem. Soc., 122:3274-3287, 2000.

Petersheim, M. and Turner, D.H., "Base-stacking and base-pairing contributions to helix stability: thermodynamics of double-helix formation with CCGG, CCGGp, CCGGAp, ACCGGp, CCGGUp, and ACCGGUp," Biochemistry, 22(2):8 pages, 1983.

Peyret et al., "Nearest-neighbor thermodynamics and NMR of DNA sequences with internal A•A, C•C, G•G, and T•T mismatches," Biochemistry, 38:3468-3477, 1999.

Ren et al., "Naphthalene, Phenanthrene, and Pyrene as DNA Base Analogues: Synthesis, Structure and Fluorescence in DNA," J. Am. Chem. Soc. 118 (33), pp. 7671-7678, (1996).

Roberts et al., "Theoretical and Experimental Study of Isoguanine and Isocytosine: Base Pairing in an Expanded Genetic System," J. Am. Chem. Soc., 4640-4649, 1997.

Santalucia, J., Allawi, H. and Seneviratne, P.A., "Improved nearest-neighbor parameters for predicting DNA duplex stability," Biochemistry, 35:3555-3562, 1996.

Switzer et al., "Enzymatic Recognition of the Base Pair between Isocytidine and Isoguanosine", Biochemistry, 32(39):10489-10496, (1993).

Taylor et al., "Flow cytometric platform for high-throughput single nucleotide polymorphism analysis," BioTechniques, 30(3):661-669, Mar. 2001.

The Stratagene Catalog, "Gene Characterization Kits," 1988, pp. 39.

Tor et al., "Site Specific Enzymatic Incorporation of an Unnatural Base, N6-(6-Aminohexyl)isoguanosine into RNA", J. Am. Chem. Soc., 115:4461-4467,1993.

Walker et al., "Isothermal in vitro amplification of DNA by a restriction enzyme/DNA polymerase system," Proc. Nat'l Acad; Sci., 89:392-396, Jan. 1992.

Whitcombe, et al. "Detection of PCR Products Using Self-Probing Amplicons and Fluorescence," Nature Biotech, 17(8):804-807, Aug. 1999.

International Preliminary Report on Patentability, issued in International Patent No. PCT/US2010/053773, mailed on Apr. 24, 2012.

Chun et al., "Dual priming oligonucleotide system for the multiplex detection of respiratory viruses and SNP genotyping of CYP2C19 gene," *Nucleic Acids Research*, 35(6):e40, 6 pages, 2007.

\* cited by examiner

AMPLIFICATION PRIMERS WITH NON-STANDARD BASES FOR INCREASED REACTION SPECIFICITY

CROSS-REFERENCE TO RELATED PATENT APPLICATIONS

This application claims priority to U.S. Provisional Application No. 61/254,281, filed Oct. 23, 2009, the entire contents of which are incorporated herein by reference in its entirety.

TECHNICAL FIELD

The present technology relates generally to the fields of molecular biology, recombinant DNA technology and nucleic acid amplification. More specifically, the present technology relates to the use of non-standard bases for improving specificity in amplification reactions.

BACKGROUND

Nucleic acid amplification is an important process pertaining to molecular biology. Numerous methods of nucleic acid amplification require the annealing of an oligonucleotide primer to a template nucleic acid during some stage of the process. The amplification process can result in an exponential increase of target nucleic acids. However, the success of target nucleic acid amplification hinges on the specificity in which a primer anneals to its target, i.e., its complementary sequence. Whether a primer anneals to a non-specific site or specifically to its complementary sequence depends on numerous factors including the annealing temperature, length of the primer, G/C content, pH, and secondary or tertiary structures which may be formed. Considering the plethora of variables pertaining to primer annealing specificity, it can be difficult to accurately predict which primers will specifically anneal to a target nucleic acid under certain conditions.

SUMMARY

In one aspect, the present disclosure provides a method for increasing the annealing specificity of an amplification reaction, comprising contacting a nucleic acid sample under amplifying conditions with at least one primer comprising: (a) a 3'-segment complementary to a template sequence; (b) an iso-region at the 5'-end of the 3'-segment, wherein the iso-region comprises at least two contiguous or non-contiguous non-standard bases, wherein the iso-region restricts the at least one primer's annealing locus to the 3'-segment, and wherein the at least two contiguous or non-contiguous non-standard bases are independently selected from the group consisting of: iso-C and iso-G; (c) a 5'-segment at the 5'-end of the iso-region, wherein the 5'-segment comprises a nucleotide sequence complementary to the template sequence, wherein the at least one primer has increased annealing specificity for the template sequence compared to the primer having only the 3'-segment.

In one embodiment, the at least one primer is 6 to 60 nucleotides long. In one embodiment, the iso-region comprises from about 1 to about 15 non-standard bases. In one embodiment, the amplification reaction is selected from the group consisting of: PCR; Reverse Transcriptase-PCR; Real-Time PCR; Differential Display-PCR; PCR-based genomic analysis; Arbitrary Primed-PCR; Multiplex-PCR; long-range PCR; linear PCR; inverse PCR; quantitative PCR; touchdown PCR; in situ PCR; vectorette PCR; thermal asymmetric interlaced PCR; mixed oligonucleotide-primed amplification of cDNA; 3'-Rapid Amplification of cDNA Ends; 5'-Rapid Amplification of cDNA Ends, high resolution melt analysis, and primer extension reactions.

In one embodiment, an annealing step is conducted at temperatures sufficient for increasing the annealing specificity of the at least one primer compared to a primer having only the 3'-segment.

In another aspect, the present disclosure provides a method for amplifying a target nucleic acid in a two-stage reaction comprising: (a) performing a first-stage amplification of a template sequence at a first annealing temperature to form a first amplification product, comprising at least two cycles of denaturing the template sequence, annealing at least one primer, and extending the at least one primer, wherein the at least one primer comprises: (i) a 3'-segment complementary to a template sequence; (ii) an iso-region at the 5'-end of the 3'-segment, wherein the iso-region comprises at least two contiguous or non-contiguous non-standard bases, wherein the iso-region restricts the at least one primer's annealing locus to the 3'-segment, and wherein the at least two contiguous or non-contiguous non-standard bases are independently selected from the group consisting of: iso-C and iso-G; and (iii) a 5'-segment at the 5'-end of the iso-region, wherein the 5'-segment comprises a nucleotide sequence complementary to the template sequence; and (b) performing a second-stage amplification of the first amplification product at a second annealing temperature comprising at least one cycle of: (i) denaturing the amplification product generated from step (a), annealing the at least one primer, and extending the at least one primer; or (ii) denaturing the amplification product generated from step (a), and annealing and extending a primer comprising a sequence corresponding to the 5'-segment of the at least one primer.

In one embodiment, the target nucleic acid is a cDNA formed by (a) hybridizing an oligonucleotide dT primer or an anchored oligonucleotide dT primer to a poly-A tail region of a target mRNA, or hybridizing random hexamer, heptamer, and/or octomer oligonucleotides to a target mRNA; and (b) reverse transcribing the target mRNA to produce a cDNA.

In one embodiment, the two-stage amplification procedure is applied to methods comprising the group of: PCR; multiplex DNA amplification; identification of differentially expressed genes; 3'-Rapid Amplification of cDNA Ends; 5'-Rapid Amplification of cDNA Ends; primer extension reactions; amplifying full-length cDNA; amplifying 5'-enriched cDNA; DNA fingerprinting; RNA fingerprinting; identification of conserved homology segments in multigene families; identification of nucleotide sequence variations; pre-miRNA amplification; rRNA amplification; high resolution melt analysis following PCR; and mutagenesis.

In one aspect, the present disclosure provides a method for increasing the annealing specificity of at least one primer, comprising the steps of: (a) synthesizing the at least one primer, wherein a 3'-segment is complementary to a template sequence; (b) incorporating at the 5'-end of the 3'-segment an iso-region comprising at least two contiguous or non-contiguous non-standard bases, wherein the iso-region restricts the at least one primer's annealing locus to the 3'-segment thereby increasing the annealing specificity of the 3'-segment compared to a primer having only the 3'-segment, and wherein the at least two contiguous or non-contiguous non-standard bases are independently selected from the group consisting of: iso-C and iso-G; (c) incorporating at the 5'-end of the iso-region a 5'-segment comprising a nucleotide sequence complementary to any region of a template containing the template sequence, whereby the at least one primer has increased annealing specificity for the template sequence compared to the primer having only the 3'-segment.

In one embodiment, the synthesizing comprises a method selected from the group consisting of: solid state synthesis; DNA replication; reverse transcription; restriction digestion; run-off transcription; PCR; PCR-based methods; primer extension; and ligation. In one embodiment, the at least one primer sequence is 6 to 60 deoxyribonucleotides or ribonucleotides long.

In one embodiment, the iso-region comprises from about 1 to about 15 of the non-standard bases. In one embodiment, the at least one primer is used in an amplification reaction or a two-stage amplification reaction.

DETAILED DESCRIPTION

Figure 1:
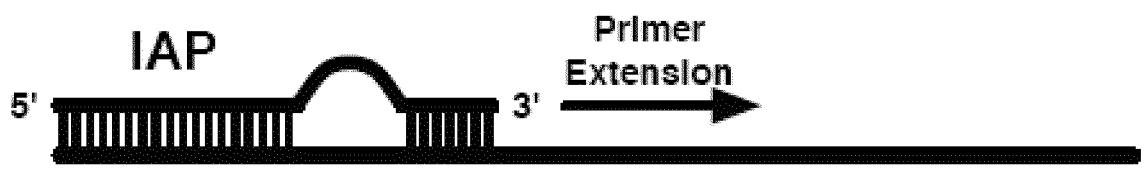
FIG. 1 is an illustrative embodiment of the methods in which the first panel shows the initial hybridization, both 5' and 3' ends hybridizing with the iso-base region indicated in the bubble. The next two panels are examples of mismatches between either the 5' or 3' regions and the template. Finally, the last panel shows the IAP hybridizing to a previously replicated strand with the isobases pairing with each other. The Tm of this priming will be very high, therefore very favorable as compared to any of the initial priming events.
Figure 1:
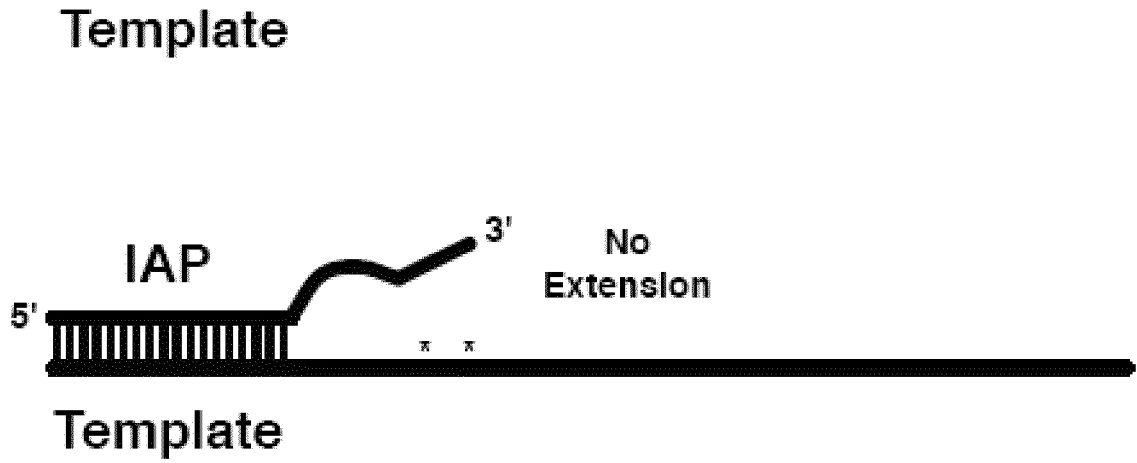
Figure 1:
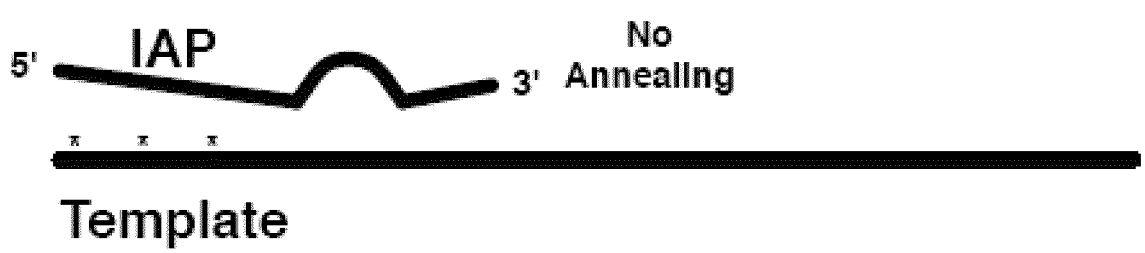
Figure 1:
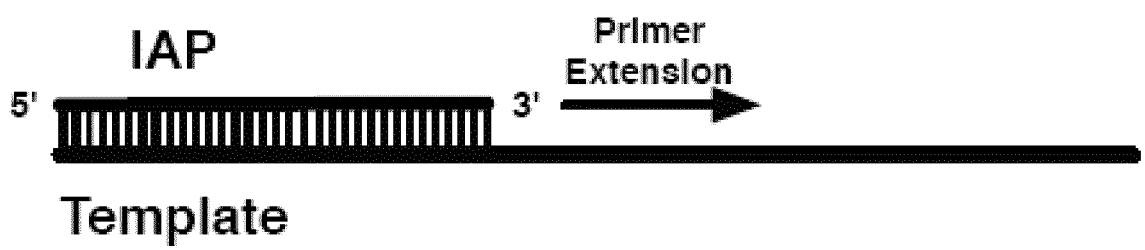

It is to be appreciated that certain aspects, modes, embodiments, variations and features of the technology are described below in various levels of detail in order to provide a substantial understanding of the present disclosure.

In practicing the present technology, many conventional techniques in molecular biology, protein biochemistry, cell biology, microbiology, and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y. (1989)); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

Units, prefixes, and symbols may be denoted in their accepted SI form. Unless otherwise indicated nucleic acid sequences are written left to right in the 5' to 3' orientation. Nucleic acids may be referred to herein by either their commonly known nomenclature or by the one-letter symbols recommended by the IUPAC-IUBMB Nomenclature Commission.

In the description that follows, a number of terms are utilized extensively. Definitions are herein provided to facilitate understanding of the technology. The terms described below are more fully defined by reference to the specification as a whole.

As used herein, the terms "a" and "an" mean "one or more" unless the singular is expressly specified.

As used herein, the term "allele" refers to a specific member of a collection of naturally occurring sequence variants (i.e., detectable within a population of individuals) at a specific genomic locus or marker.

As used herein, the terms "anchor oligonucleotide" or "anchor oligo dT" refer to an oligonucleotide sequence, i.e., an oligo or poly dT, with an "anchor" residue to ensure binding at loci or a locus of interest. For example, anchored oligo dT sequences have a number of thymidine residues, e.g., between 1-50 or 10-40 or 20-30, and, to allow hybridization at the beginning or end of an mRNA message, one or more G, C, or A nucleotide anchors positioned at the 3' end of the oligo dT. The one or more anchor residues allow for increased hybridization specificity compared to sequences without an anchor. Anchored oligo dT's are especially beneficial for reverse transcription and cDNA synthesis.

As used herein, the terms "annealing factors" or "annealing conditions" refer to elements that affect primer annealing, such as: annealing temperature; primer length; G/C content; pH; and/or secondary or tertiary structures which may be formed.

As used herein, the term "arbitrary nucleotide sequence" refers to a nucleotide sequence that is chosen without knowledge of the target nucleotide sequence.

As used herein, the terms "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

As used herein, the term "cDNA" refers to complementary DNA. Complementary DNA is synthesized via reverse transcription of a mRNA sequence thereby forming its complementary DNA sequence.

As used herein, the term "consensus sequence" refers to the nucleotide bases most often found at any given position when comparing a large number of similar nucleotide sequences.

As used herein, the term "conserved region" and "conserved region of a gene in a multigene family" refers to a segment of a gene or amino acid sequence that is significantly similar between members of gene families. The degree of similarity can vary and in some embodiments, the conserved regions will be identical between family members. In other embodiments, the nucleotide sequence may vary significantly, but will still encode for amino acid segments that are conserved between family members.

As used herein, the term "cycle" refers to the process which results in the production of a copy of a target nucleic acid. A cycle includes a denaturing step, an annealing step and an extending step, i.e., during PCR.

As used herein, the term "degenerate" sequence refers to the nucleotide sequence that is deduced from an amino acid sequence. Accordingly, a degenerate sequence can form a pool of the nucleotide sequences from one amino acid sequence due to the degeneracy of the genetic code.

As used herein, the term "excess" refers to an amount of a component(s) in a reaction, such that the ability to achieve a desired amplification is not limited by the concentration of that component.

As used herein, the term DNA or RNA "fingerprinting" refers to a set of discrete DNA amplicon products characteristic of a genome or a set of discrete cDNA segments characteristic of a mRNA sample.

As used herein, the term "genomic DNA" or "gDNA" refers to a population of DNA that includes the complete genetic component of a species. Thus, genomic DNA includes the complete set of genes present in a pre-selected species. The complete set of genes in a species is also referred to as the "genome."

As used herein, the term "high resolution melt analysis" or "HRM" refers to the technique of oligonucleotide identification that utilizes post-PCR melt analysis, i.e., strand separation or denaturation, to determine the temperature at which specific PCR amplicons melt or separate. In this regard, the amplicon sequence can be confirmed or determined based on melting temperature, in addition to other factors, if necessary.

As used herein, the terms "hybridization" or "annealing" are used in reference to the pairing of complementary nucleic acids. Hybridization and the strength of hybridization (i.e., the strength of the association between the nucleic acids) is influenced by the degree of complementarity between the nucleic acids, stringency of the hybridization conditions involved, the melting temperature of the formed hybrid, the G/C ratio within the nucleic acids, and other annealing factors.

As used herein, the term "interrogation position" refers to the location of a specific nucleotide base of interest within a target nucleic acid. For example, in the analysis of single nucleotide polymorphisms, the interrogation position in the target nucleic acid is the position which would be different from the wild type position. The interrogation position also includes the location of a nucleotide sequence within a primer which is complementary to an interrogation position of the target sequence.

As used herein, the acronym "IAP" refers to an Iso-base Amplification Primer. IAPs are a set of primers containing an iso-region which separates a 3'-segment from a 5'-segment.

As used herein, the term "iso-region" refers to the segment of an IAP between the 3'- and 5'-target binding segments which includes at least two contiguous or non-contiguous non-standard bases, such as iso-C and/or iso-G. The iso-region is responsible for the specified annealing function of an IAP in association with annealing temperature, length of the primer, G/C content, pH, and secondary or tertiary structures which may be present. The iso-region also defines the 3'- and 5'-segments of the IAP.

As used herein, the term "mRNA" refers to messenger RNA. Messenger RNA is ribonucleic acid which is transcribed from a template DNA sequence.

As used herein, the term "multiplex PCR" refers to the simultaneous amplification of multiple DNA targets in a single reaction vessel.

As used herein, "nucleic acids" include polymeric molecules such as deoxyribonucleic acid (DNA), ribonucleic acid (RNA), peptide nucleic acid (PNA), or any sequence of what are commonly referred to as bases joined by a chemical backbone where the bases have the ability to form base pairs or hybridize with a complementary chemical structure. Suitable non-nucleotidic backbones include, for example, polyamide and polymorpholino backbones. The term "nucleic acids" includes oligonucleotide, nucleotide, or polynucleotide sequences, and fragments or portions thereof. The nucleic acid can be provided in any suitable form, e.g., isolated from natural sources, recombinantly produced, or artificially synthesized, can be single- or double-stranded, and can represent the sense or antisense strand.

As used herein, the term "oligonucleotide" refers generally to short chain (e.g., less than 100 nucleotides in length, and typically about 6 to 60 nucleotides in length) nucleic acids that can be prepared using techniques presently available in the art such as, solid support nucleic acid synthesis, DNA replication, reverse transcription, restriction digest, run-off transcription, or the like. The exact size of the oligonucleotide will depend upon many factors, which in turn will depend upon the ultimate function or use of the oligonucleotide.

As used herein, the term "polymorphic" refers to the condition in which two or more variants of a specific genomic sequence can be found in a population.

As used herein, the term "polymorphic site" is the locus at which a genetic or proteomic variation occurs. A "single nucleotide polymorphism," or "SNP," is a single base-pair variant, typically, when one nucleotide is substituted for another nucleotide at a polymorphic site. Deletion of a single nucleotide or insertion of a single nucleotide may also give rise to single nucleotide polymorphisms. The polymorphic site may be occupied by two different nucleotides.

As used herein, the term "polymorphism" refers to the presence of two or more alternative genomic sequences or alleles between or among different genomes or individuals.

As used herein, the term "pre-selected arbitrary nucleotide sequence" refers to any defined or pre-selected deoxyribonucleotide, ribonucleotide, or mixed deoxyribonucleotide and/or ribonucleotide sequence which contains a particular sequence of natural and/or non-standard bases.

As used herein, the term "primer" refers to an oligonucleotide, whether occurring naturally or produced synthetically, which is capable of acting as a point of initiation for nucleotide synthesis. In general, the primer is a single-stranded oligonucleotide which may contain naturally occurring nucleotides, modified nucleotides, or non-standard bases. Additionally, a "standard primer", as referred to in the context of IAP amplification reactions, or any other reaction, refers to any primer that is not an IAP primer, e.g., the standard primer includes only natural oligonucleotides or other bases that are not iso-bases.

As used herein, the term "priming" refers to the positioning of an oligonucleotide or nucleic acid to a template sequence whereby the positioning enables a polymerase to polymerize nucleotides into a nucleic acid molecule which is complementary to the template sequence or region thereof.

As used herein, the term "sample" is used in its broadest sense. The term includes a specimen or culture (e.g., microbiological cultures), as well as biological and non-biological samples.

As used herein, the term "segment" is used in conjunction with an IAP which refers to a nucleotide sequence separated by an iso-region. As used herein, the term "3'-segment" or "5'-segment" refers to a nucleotide sequence at the 3'-end or 5'-end of an IAP, respectively, which is separated by an iso-region, and which is capable of specifically hybridizing to a complementary region of a target nucleic acid.

As used herein, the term "sequence" refers to an ordered arrangement of nucleic acids.

As used herein, the term "target nucleic acid", "target sequence" or "target nucleotide sequence" refers to a nucleotide sequence of interest which is the subject of amplification or detection under the parameters described.

As used herein, the term "template" refers to nucleic acids or polymers thereof. The IAP can be employed in nucleic acid amplification using single or double-stranded nucleic acids as a template.

As used herein, "Tm" refers to the melting temperature at which half of the designated primers are annealed to a target nucleic acid or region.

I. Methods for Increased Amplification Reactions Using Non-Standard Bases and Applications Thereof One aspect of the present technology relates to IAPs for use in amplification of nucleic acid sequences and applications thereof. IAPs allow for primer annealing to be controlled in association with numerous factors, e.g., annealing temperature, primer length, G/C content, pH, and secondary or tertiary structures which may be formed, i.e., "annealing factors", wherein the specificity of nucleic acid amplification is significantly improved. The principle behind an IAPs increased annealing specificity is based on the composition of an oligonucleotide primer having distinct 3'- and 5'-segments separated by an iso-region (See FIG. 1). The iso-region positioned between the 3'- and 5'-segments acts as a regulator which controls template annealing in association with the annealing factors described herein. The presence of the iso-region precludes annealing of the 5'-segment and concomitantly restricts IAP annealing to the 3'-segment which results in a dramatic improvement of annealing specificity. Non-standard bases, i.e., iso-bases, positioned between the 3'- and 5'-segments define the iso-region which coordinately defines each segment. Accordingly, IAPs are fundamentally different from conventional primers whereby IAPs have a greater annealing specificity, compared to conventional primers, in association with annealing factors. Similarly, IAPs also have increased sensitivity in subsequent amplification cycles, compared to conventional primers, wherein iso-bases more favorably base-pair with their complementary iso-base compared to any other base or base substitution.

In one embodiment, the presence of one or more non-standard bases positioned between the 3'- and 5'-segments restricts IAP annealing to the 3'-segment. Accordingly, the annealing sequence of a primer can be precisely controlled which makes it possible to design a primer with a desired annealing sequence. In another embodiment, IAPs are useful when an annealing segment of a primer must be specifically limited, e.g., SNP genotyping, DNA microarray screening, and detection of differentially expressed genes.

In another embodiment, the presence of non-standard bases positioned between the 3'- and 5'-segment precludes the 5'-segment from annealing to a template under conditions allowing for the 3'-segment to anneal to the template sequence. Accordingly, the 5'-segment does not form nucleation sites with complementary nucleotides from the template thereby increasing the annealing specificity of the 3'-segment. Consequently, the specificity of primer annealing is highly sensitive whereas even a single-base mismatch can be discerned. In one embodiment, IAPs are particularly useful for the identification of a nucleotide variation in a target nucleic acid including SNPs and point mutations.

A. General Application of IAPs to Amplification

In one aspect of the present technology, the disclosure contemplates a method for increasing the annealing specificity of an amplification reaction which includes, but is not limited to:

(a) a 3'-segment complementary to a template sequence; and (b) an iso-region at the 5'-end of the 3'-segment, wherein the iso-region includes at least two contiguous or non-contiguous non-standard bases, wherein the iso-region restricts the primer's annealing locus to the 3'-segment thereby increasing the annealing specificity of the 3'-segment compared to a primer having only the 3'-segment, and wherein the at least two contiguous or non-contiguous non-standard bases are independently selected from the group of: iso-C and iso-G; and (c) a 5'-segment at the 5'-end of the iso-region, wherein the 5'-segment contains a nucleotide sequence complementary to any region of a template containing the template sequence, wherein the primer has increased annealing specificity for the template sequence compared to the primer having only the 3'-segment.

In one embodiment, IAPs comprise an oligonucleotide primer having distinct 3'- and 5'-segments separated by an iso-region containing at least two contiguous or non-contiguous non-standard bases, i.e., iso-C and/or iso-G. The presence of iso-C and/or iso-G in an IAP generates lower annealing temperatures compared to conventional primers, whereby the non-standard bases have weaker hydrogen bonding interactions with natural bases. However, the presence of contiguous or noncontiguous non-standard bases within an iso-region forms a boundary between the 3'- and 5'-segments thereby affecting the annealing specificity of each region. Accordingly, the 3'-segment can specifically anneal to a target nucleic acid whereas the iso-region precludes the 5'-segment from annealing. Consequently, the annealing specificity of the IAP is increased compared to a conventional primer.

In one embodiment, the IAP contains at least 1, at least 2, at least 3, at least 4, at least 5, at least 6, at least 7, at least 8, at least 9, or at least 10 non-standard bases between the 3'- and 5'-segments, i.e., the iso-region. In one embodiment, a minimum number of non-standard bases within the iso-region may be required to disrupt the annealing of the 5'-segment to the template. In another embodiment, the iso-region contains up to 15 non-standard bases. In some embodiments, the iso-region contains only iso-C or iso-G. In other embodiments, the iso-region contains both iso-C and iso-G. In other embodiments, the iso-region may contain one or more standard bases that are not capable of binding to the target sequence. In one embodiment, the iso-region may contain natural bases separating the iso-bases, i.e., to form the non-contiguous IAP primers. In one embodiment, at least about 1, 2, 3, 4, 5, 6, 7, 8, 9, or 10 natural bases separate one or more iso-bases in a non-contiguous IAP primer. In one embodiment, a single natural base, e.g., G, A, T, C, or U, separates one or more iso-bases in a non-contiguous IAP primer.

The iso-region may have a particular configuration of standard and non-standard bases, which include, but are not limited to, the following embodiments, wherein "I" denotes a non-standard base, i.e., an iso-base, and "N" denotes any standard base, i.e., G, A, T, C, or U:

-I-I-; -I-N-I-; -I-I-N-; -N-I-I-; -I-I-I-; -I-N-I-N-; -N-I-N-I-; -N-I-I-N-; -N-N-I-I-; -I-I-N-N-; -I-I-I-N-; -I-N-I-I-; -I-I-N-I-; -N-I-I-I-; -I-I-I-I-, etc.

In one embodiment, the length of an IAP or oligonucleotide primer may be restricted by determining the desired annealing specificity required to hybridize to a template. In one embodiment, a 20 nucleotide IAP or oligonucleotide primer is more specific than an IAP or oligonucleotide primer containing 10 nucleotides, and the addition of each nucleotide to an IAP or oligonucleotide primer increases the annealing temperature.

In one embodiment, the 3'- and 5'-segment lengths may vary depending on the objective of each application. In another embodiment, the 3'-segment is the minimal required length for primer annealing, i.e., 6 nucleotides. Additionally, the 3'-segment sequence may vary from 10 to 25 nucleotides and may contain up to 60 nucleotides in length. In another embodiment, the 3'-segment may include ribonucleotides or deoxyribonucleotides.

In one embodiment, the 5'-segment is the minimal required length for primer annealing, i.e., 6 nucleotides. In another embodiment, the 5'-segment may be up to 60 nucleotides in length. In one embodiment, the 5'-segment includes 6 to 60 nucleotides. In one embodiment, the entire IAP may contain 35 to 50 nucleotides, but may also contain up to about 100 nucleotides in length.

In one embodiment, the 5'-segment contains a pre-selected arbitrary nucleotide sequence not complementary to any site on a template. Consequently, the pre-selected sequence serves as a priming site for subsequent amplification. In one embodiment, the 5'-segment pre-selected arbitrary nucleotide sequence is composed of a T3 promoter sequence, T7 promoter sequence, SP6 promoter sequence, or a M13 forward or reverse sequence. In another embodiment, a longer arbitrary sequence is used, i.e., approximately 10 to 60 bases, at the 5'-segment. Longer sequences may reduce the amplification efficiency of an IAP, however, shorter sequences, i.e., approximately 15 to 17 bases, may reduce the efficiency of annealing under stringent conditions.

In one embodiment of the present technology, design modifications of the 5'-segment are contemplated unless the modifications negate the advantages of the IAP, i.e., improvement in annealing specificity. For example, the 5'-segment may include, but is not limited to, sequences recognized by restriction endonucleases making it possible to clone an amplified product. In one embodiment, the 5'-segment may contain at least one nucleotide with a label for detection or isolation of an amplified product. Labels may include, but are not limited to, fluorophores, chromophores, chemiluminescers, magnetic particles, radioisotopes, mass labels, electron dense particles, enzymes, cofactors, substrates for enzymes, and haptens having specific binding partners, e.g., an antibody, streptavidin, biotin, digoxigenin, and chelating groups. In one embodiment, the 5'-segment may also include a bacteriophage RNA polymerase promoter region.

The advantageous properties of IAPs may be applied to various amplification methods and include, but are not limited to: amplifying a nucleic acid sequences; amplifying a target nucleic acid sequence; multiplex DNA amplification; the identification of differentially expressed genes; rapid amplification of cDNA ends (RACE); amplifying full-length cDNA; amplifying 5'-enriched cDNA; DNA or RNA fingerprinting; the identification of conserved homology segments in multigene families; identification of nucleotide sequence variations; application to mutagenesis; primer extension reactions; and other applications.

B. Applications for Amplifying a Target Nucleic Acid

In one embodiment, IAPs are applied to Polymerase Chain Reaction ("PCR") amplification techniques. PCR may be performed under a first and a second annealing temperature, i.e., under different stringencies. In one embodiment, the first annealing temperature may be equal to or lower than the second annealing temperature. Accordingly, the second annealing temperature may be higher than the first annealing temperature. In a PCR process performed under two different annealing temperatures, the 3'-segment is annealed to a template sequence at the first annealing temperature and the incorporated 5'-segment serves as a priming site during the second amplification stage, i.e., second annealing temperature.

In one embodiment, the iso-region is composed of at least two contiguous or non-contiguous non-standard bases. The iso-region has a lower melting temperature ("Tm") than the 3'- or 5'-segments due to weaker hydrogen bonding between the iso-bases and the standard base pairs of the template. It is not energetically favorable for the iso-region to anneal to the template under conditions allowing for the 3'-segment to anneal at the first annealing temperature. Consequently, the presence of the iso-region restricts primer annealing to the 3'-segment at the first annealing temperature. Accordingly, the 5'-segment does not form nucleation sites with complementary nucleotides from the template at the first annealing temperature, thereby hindering the 3'-segment from annealing. Thus, the 3'-segment anneals more specifically in the presence of the 5'-segment at the first annealing temperature because the 3'-segment is selectively bound to its complementary sequence.

In one embodiment, the 5'-segment includes a pre-selected arbitrary nucleotide sequence which serves as a priming site during the second stage of amplification, i.e., the second annealing temperature. These conditions allow for subsequent amplification of reaction products generated from annealing and extension of the 3'-segment. Accordingly, only the reaction products generated from annealing and extension of the 3'-segment sequence can be amplified at a theoretical optimum, i.e., a two-fold product increase for each PCR cycle under the second annealing temperature. Thus, the 3'-segment serves as an annealing site to the template sequence at the first annealing temperature and the 5'-segment is used as a priming site at the second annealing temperature for subsequent amplification of the product. It will be readily apparent to the skilled artisan that IAPs are useful in a variety of primer-based nucleic acid amplification methods including, but not limited to, Ligase Chain Reaction ("LCR"); Polymerase Ligase Chain Reaction; Gap-LCR; Repair Chain Reaction; and Nucleic Acid Sequence Based Amplification ("NASBA").

In another aspect of the present technology, the disclosure provides for a method of amplifying a target nucleic acid from a mixture of nucleic acids using at least one IAP. In one embodiment, the 3'-segment contains a sequence complementary to the target nucleic acid to hybridize therewith.

In one embodiment, the disclosure contemplates a method using a two-stage amplification procedure, wherein a target nucleic acid is amplified from a mixture of nucleic acids, which includes, but is not limited to, the steps of:

(a) performing a first-stage amplification of the target nucleic acid at a first annealing temperature including at least two cycles of primer annealing, primer extending, and denaturing, whereby the first IAPs contain a 3'-segment complementary to the target nucleic acid under conditions in which the first IAPs anneal to the target nucleic acid thereby producing amplified products; and (b) performing a second-stage amplification of the products generated from step (a) at a second annealing temperature including at least one cycle of primer annealing, primer extending, and denaturing, using the same primers, i.e., IAPs, from step (a) or primers containing a pre-selected arbitrary nucleotide sequence corresponding to each 5'-segment of the primers used in step (a) under conditions allowing for the primers to anneal to the 3'- and 5'-ends of the amplification products, respectively. Accordingly, the amplified products from step (a) are re-amplified.

In one embodiment, a method is provided for employing a two-stage amplification process for selectively amplifying a target mRNA sequence which includes, but is not limited to, the steps of:

(a) contacting the mRNA with an oligonucleotide dT ("oligo dT") primer or an anchored oligo dT primer, which may be an IAP, for hybridization to the mRNA poly-A tails under conditions sufficient for template driven DNA synthesis to occur; and (b) reverse transcribing the mRNA to produce a first cDNA strand; and (c) performing a first-stage amplification of the target nucleic acid from the first cDNA strand obtained from step (b) at a first annealing temperature including at least two cycles of primer annealing, primer extending, and denaturing, wherein the IAPs contain a 3'-segment complementary to a region of the target nucleic acid to hybridize therewith; and (d) performing a second-stage amplification of the amplification products generated from step (c) at a second annealing temperature including at least one cycle of primer annealing, primer extending, and denaturing, using the same primers, i.e., IAPs, as used in step (c) or primers containing a pre-selected arbitrary nucleotide sequence corresponding to each 5'-segment of the primers used in step (c), under conditions allowing for the primers to anneal to the 3'- and 5'-ends of the amplification products, respectively. Accordingly, the amplified products from step (c) are re-amplified.

In one embodiment, the present technology discloses methods for amplifying a target nucleic acid from any desired nucleic acid molecule, i.e., DNA or RNA. The DNA or RNA molecule may be in double-stranded or single-stranded form. Where the nucleic acid starting material is double-stranded, the two strands may be separated into single-strands or partially single-stranded form. In one embodiment, methods for separating nucleotide strands include, but are not limited to, heating, alkali, formamide, urea and glycoxal treatment, enzymatic methods, e.g., helicase action, and/or applying single-stranded binding proteins, i.e., SSB or RPA. For example, strand separation can be achieved by heating a nucleotide molecule at temperatures ranging from 80° C. to 105° C. See e.g., Sambrook, et al., *Molecular Cloning, A Laboratory Manual*, Cold Spring Harbor Laboratory Press, Cold Spring Harbor, NY (2001). In one embodiment, target nucleic acids are not required to contain any particular sequence or length.

In another embodiment, molecules which may be amplified include, but are not limited to, any naturally occurring prokaryotic, eukaryotic (i.e., protozoans, parasites, fungi, yeast, higher plants, lower and higher animals, including mammals and humans), viral (i.e., herpes viruses, HIV, influenza virus, Epstein-Barr virus, hepatitis virus, polio virus, etc.), or viroid nucleic acid. In one embodiment, the nucleic acid molecule may contain any sequence which has been or can be chemically synthesized.

In one embodiment, IAPs are hybridized to a template region forming a double-stranded structure. See e.g., Sambrook, et al., *Molecular Cloning, A Laboratory Manual*, Cold Spring Harbor Laboratory Press, Cold Spring Harbor, N.Y. (2001); Haymes et al., *Nucleic Acid Hybridization, A Practical Approach*, IRL Press, Washington, D.C. (1985). In one embodiment, the 3'-segment is only capable of forming a stable double-stranded structure. Accordingly, a fully complementary 3'-segment sequence is not required as long as hybridization occurs thereby forming a double-stranded structure. However, IAP hybridization to a target nucleic acid is a prerequisite for template-dependent polymerization. See e.g., Sambrook, et al., *Molecular Cloning, A Laboratory Manual*, Cold Spring Harbor Laboratory Press, Cold Spring Harbor, N.Y. (2001); Haymes et. al., *Nucleic Acid Hybridization, A Practical Approach*, IRL Press, Washington, D.C. (1985). In one embodiment, the nucleotide composition of the IAP can affect the temperature at which annealing is optimal, thereby affecting its priming efficiency.

A variety of DNA polymerases can be used in the amplification step of the present methods. In one embodiment, Klenow fragment of *E. coli* DNA polymerase I or bacteriophage T7 DNA polymerase may be used. In another embodiment, the polymerase is a thermostable DNA polymerase selected from the group which includes, but is not limited to: *Thermus aquaticus* (Taq); *Thermus thermophilus* (Tth); *Thermus filiformis; Thermis flavus; Thermococcus literalis*; or *Pyrococcus furiosus* (Pfu). The polymerases can be isolated from bacteria or commercially obtained. In one embodiment, the polymerases can be obtained from cells expressing the polymerase. In one embodiment, when performing a polymerization reaction, the required components are supplied in excess for each reaction. In one embodiment, the reaction mixture contains a required amount of cofactors such as $Mg^{2+}$, dATP, dCTP, dGTP, dTTP, and/or non-standard nucleotide triphosphates complementary to the non-standard bases present in the iso-region in sufficient quantities to support the degree of amplification desired.

It will be readily understood by the skilled artisan that the 5'-segments used in the first-stage amplification may contain identical or different sequences. In one embodiment, the 5'-segment sequences are identical and one primer corresponding to the 5'-segment sequence will be used in the second-stage amplification. In another embodiment, the 5'-segment sequences differ and two primers, each corresponding to the sequence of each 5'-segment, will be used during the second-stage amplification.

In another embodiment, the present technology includes a process for selectively amplifying a target nucleic acid or a template or mixture thereof, using an IAP, wherein a set of primers containing an IAP and a conventional or standard primer may be used in the first amplification step. Accordingly, the conventional or standard primer is added with the IAP only to the first amplification step. Consequently, only one pre-selected arbitrary primer corresponding to the 5'-segment sequence of the IAP is added to the second amplification step. In one embodiment, this process may be used when the IAP 3'-segments used in the first amplification step have different melting temperatures.

In one embodiment, the second-stage amplification step entails using the complete IAP sequences used in the first-stage amplification step opposed to primers corresponding to the 5'-segments of the IAPs. In this regard, the present embodiment does not require further addition of the primers corresponding to the IAP 5'-segments to the reaction mixture at the time of, or subsequent to, the first-stage amplification step.

In one embodiment, the first annealing temperature ranges from 30° C. to 68° C. or from 40° C. to 65° C. In one embodiment, the second annealing temperature ranges from 50° C. to 72° C. In another embodiment, the first annealing temperature is equal to or lower than the second annealing temperature. In one embodiment, the length or Tm of the 3'-segment will determine the annealing temperature for the first-stage amplification.

In one embodiment, the first-stage amplification is performed for at least 2 cycles of annealing, extending, and denaturing to improve the specificity of primer annealing during the first-stage amplification, and through subsequent cycles. Accordingly, the second-stage amplification effectively proceeds under high stringent conditions, i.e., under higher temperatures. In one embodiment, the first-stage amplification can be performed for 2 to 30 cycles. In another embodiment, the second-stage amplification can be performed for at least one cycle and up to 45 cycles, wherein the first-stage product is amplified. In one embodiment, the second-stage amplification is performed for 25-35 cycles. It will be readily apparent to the skilled artisan that high and low stringency conditions may be varied for a desired application.

The present technology may be combined with other processes known in the art to achieve a specific aim. In one embodiment, following the second-stage amplification, amplified products may be isolated or purified by gel electrophoresis, column chromatography, affinity chromatography, or hybridization. In one embodiment, the amplified product may be inserted into a suitable cloning vector for applications thereof. In another embodiment, the amplified product may be expressed in a suitable host harboring an expression vector. In one embodiment, the amplified product may be placed under the control of a promoter. Accordingly, the promoter may be originated from the vector itself or a segment of the amplified product, i.e., the IAP 5'-segment. In one embodiment, a prokaryotic host promoter includes, but is not limited to, a lambda promoter, tryptophan promoter, lactose promoter and/or the T7 promoter. In another embodiment, a eukaryotic host promoter includes, but is not limited to, a metallothionein promoter, adenovirus late promoter, vaccinia virus 7.5K promoter, and promoters derived from polyoma, adenovirus 2, SV40, and/or cytomegalovirus. In one embodiment, examples of prokaryotic hosts include, but are not limited to, *E. coli, B. subtilis*, and enterobacteriaceae such as, *Salmonella typhimurium, Serratia marcescens*, and *Pseudomonas*. In addition to microorganisms, cell cultures derived from multicellular organisms may also be employed as hosts. In one embodiment, and in addition to mammalian cell hosts, insect cell systems infected with recombinant virus expression vectors, e.g., baculovirus, and plant cell systems infected with recombinant virus expression vectors, e.g., cauliflower mosaic virus or tobacco mosaic virus, or transformed with recombinant plasmid expression vectors, e.g., Ti plasmid, containing one or more coding sequences may be used. Accordingly, the expressed polypeptide from an amplified product may be purified in accordance with methods well known in the art.

C. Application to Multiplex DNA Amplification

Another aspect of the present technology discloses a method for amplifying more than one target nucleic acid, wherein more than one pair of primers are used in the same reaction. In one embodiment, annealing occurs at various temperatures to allow for DNA-DNA hybridization to occur. Accordingly, IAPs are ideal for the optimization of multiplex DNA amplification due to the high specificity of annealing/amplification at high temperatures.

In one embodiment, a method is disclosed for simultaneously amplifying more than one target nucleic acid by using more than one pair of primers in the same reaction. Accordingly, the present method includes an amplification reaction wherein at least one IAP is used. In another embodiment, the two-stage amplification procedure, as described herein, is applied to multiplex PCR. It will be readily apparent to the skilled artisan how to vary the procedure to suit the required use.

In another embodiment, the amplified products from each target nucleic acid have different molecular weights. Accordingly, the amplification products of multiplex target nucleic acids may be analyzed via size separation. In one embodiment, size separation may be performed using a variety of methods known in the art such as, but not limited to, polyacrylamide gel electrophoresis ("PAGE") or agarose gel electrophoresis, followed by nucleotide sequencing, capillary electrophoresis, and/or mass spectrometry.

D. Application to Identification of Differentially Expressed Genes

In one embodiment, the present technology discloses a method using IAPs for detecting and cloning cDNA from differentially expressed mRNAs in two or more nucleic acid samples. In another aspect of the technology, the method entails reverse transcribing the mRNA and performing an amplification reaction using at least one IAP. In one embodiment, the IAP is complementary to a region of the cDNA strand generated from reverse transcription. In another embodiment, the technology employs the two-stage amplification procedure, described herein, as applied to identification of differentially expressed genes.

In one embodiment, a method of using two-stage amplification for the identification of differentially expressed genes includes, but is not limited to:

(a) a first sample of nucleic acids representing a first population of mRNA transcripts and a second sample of nucleic acids representing a second population of mRNA transcripts; and (b) separately contacting each of the first and second nucleic acid samples with IAPs, wherein the 3'-segment of the first primer, i.e., the first IAP, contains a complementary sequence to a first site in the differentially expressed mRNA to hybridize therewith, under conditions sufficient for template driven DNA synthesis to occur; and (c) reverse transcribing the differentially expressed mRNAs whereby the first primer hybridizes to produce a population of first cDNA strands that are complementary to the differentially expressed mRNA in the first nucleic acid sample to which the first primer hybridizes, and a second population of first cDNA strands that are complementary to the differentially expressed mRNA in the second nucleic acid sample to which the first primer hybridizes; and (d) purifying and quantifying each of the first and second populations of first cDNA strands; and (e) performing a first-stage amplification of each of the first and second populations of first cDNA strands obtained from step (d) at a first annealing temperature including at least one cycle of primer annealing, primer extending, and denaturing, and using a second IAP wherein its 3'-segment is complementary to a second site in the first and second populations of first cDNA strands under conditions in which the second primer, i.e., the second IAP, anneals to the second site in each population of the first cDNA strands whereby first and second populations of second cDNA strands are generated; and (f) performing a second-stage amplification of each second cDNA strand generated from step (e) at a second annealing temperature, including at least two cycles of primer annealing, primer extending, and denaturing, using the same first and second primers, i.e., first and second IAPs, from steps (b) and (e), respectively, or a primers containing a pre-selected arbitrary nucleotide sequence corresponding to each 5'-segment of the first and second primers used in steps (b) and (e), respectively, under conditions in which the primers anneal to the 3'- and 5'-end sequences of each second cDNA strand, respectively, whereby amplification products of the second cDNA strands are generated; and (g) comparing the presence or level of individual amplification products in the first and second populations of amplification products obtained from step (f).

In one embodiment, the nucleic acid sample representing a population of mRNA transcripts can be obtained from a wide variety of biological materials. In one embodiment, the first nucleic acid sample contains mRNA expressed in a first cell and the second nucleic acid sample contains mRNA expressed in a second cell. In another embodiment, the first nucleic acid sample contains mRNA expressed in a cell at a first developmental stage and the second nucleic acid sample contains mRNA expressed in a cell at a second developmental stage, i.e., a later stage. In one embodiment, the first nucleic acid sample contains mRNA expressed in a tumorigenic cell and the second nucleic acid sample contains mRNA expressed in a normal cell.

In one embodiment, steps (e) and (f) as described above, may be performed in a single tube using the same reaction mixture except for the primers. Accordingly, steps (e) and (f) differ only with respect to time. It will be understood by the skilled artisan that primers corresponding to the 5'-segment can be added to the reaction mixture during or after second cDNA strand synthesis. In one embodiment, the primers corresponding to the 5'-segment are added to the reaction mixture immediately following step (e), followed by PCR amplification of the second cDNA strands. It will be readily understood by the skilled artisan that the 5'-segment sequences of the first and second IAPs used in steps (b) and (e), respectively, can be identical or different sequences, as previously described herein.

In one embodiment, the cDNA pools synthesized by the first IAP in step (d) can be purified and quantified by techniques well known in the art. In one embodiment, quantifying the products is necessary to control the input of the amplification step which may subsequently be compared to the final amplified products, i.e., comparison between two or more samples. In one embodiment, the amount of cDNA is measured via ultraviolet ("UV") spectroscopy or other spectrophotometric techniques known in the art.

In one embodiment, comparing the presence or level of amplified products obtained from step (f) may be performed in accordance with various methods known in the art. In one embodiment, each of the first and second populations of amplified product from step (f) are resolved by electrophoresis to identify differentially expressed mRNAs. In another embodiment, the resultant PCR-cDNA fragments are detected on an ethidium bromide-stained agarose gel. It will be readily understood by the skilled artisan that the methods disclosed herein relating to: increasing primer annealing specificity; detecting rare mRNAs; generating long-distance PCR products; increasing the speed of analysis; and allowing the rational design of a representative set of primers may be adjusted for an intended use, such as, but not limited to, mRNA, micro-RNA (miRNA), pre-miRNA, primary miRNA, rRNA, and/or snRNA amplification and detection.

II. Non-Standard Bases

As contemplated by the present technology, an IAP contains at least two contiguous or non-contiguous non-standard bases in addition to standard bases, i.e., natural bases. Natural bases, i.e., DNA and/or RNA, can form oligonucleotide templates which include deoxyriboses or riboses, respectively, coupled by phosphodiester bonds. Each deoxyribose or ribose includes a base coupled to a sugar. The natural bases incorporated in naturally-occurring DNA and RNA are adenosine (A), guanosine (G), thymidine (T), cytidine (C), and uridine (U). According to the rules of base pairing elaborated by Watson and Crick, the natural bases can hybridize to form purine-pyrimidine base pairs, wherein G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donors and hydrogen bond acceptors. The hydrogen bonds of the base pair are each formed by the interaction of at least one hydrogen bond donor on one base with a hydrogen bond acceptor on the other base. Hydrogen bond donors include heteroatoms, e.g., oxygen or nitrogen, which have at least one attached hydrogen. Hydrogen bond acceptors include heteroatoms, e.g., oxygen or nitrogen, which have a lone pair of electrons.

The natural bases, A, G, C, T, and U, can be derivatized by substitution at non-hydrogen bonding sites to form modified natural bases. For example, a natural base can be derivatized for attachment to a support by coupling a reactive functional group, e.g., thiol, hydrazine, alcohol, amine, and the like, to a non-hydrogen bonding atom of the base. Other possible substituents include, e.g., biotin, digoxigenin, fluorescent groups, alkyl groups (methyl or ethyl), and the like.

Non-natural bases, which form hydrogen-bonding base pairs, can also be constructed as described, for example, in U.S. Pat. Nos. 5,432,272; 5,965,364; 6,001,983; 6,037,120; U.S. published application no. 2002/0150900; and U.S. patent application Ser. No. 08/775,401, all of which are incorporated herein by reference. Suitable bases and their corresponding base pairs may include the following bases in base pair combinations (iso-C/iso-G, K/X, H/J, and M/N):

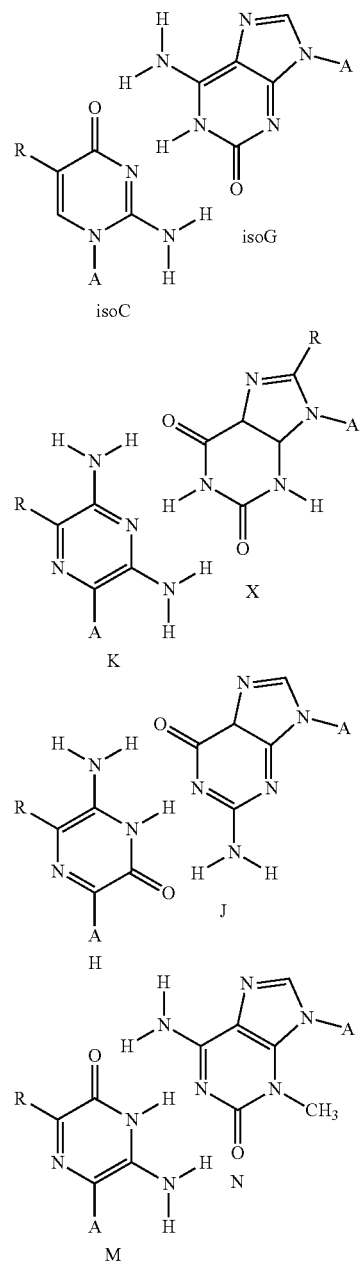

where A is the point of attachment to the sugar or other portion of the polymeric backbone and R is H or a substituted or unsubstituted alkyl group. It will be recognized that other non-natural bases utilizing hydrogen bonding can be prepared, as well as modifications of the above-identified non-natural bases by incorporation of functional groups at the non-hydrogen bonding atoms of the bases.

In another embodiment, the hydrogen bonding of the non-standard base pairs is similar to those of the natural bases where two or three hydrogen bonds are formed between hydrogen bond acceptors and hydrogen bond donors of the pairing non-standard bases. One of the differences between the natural bases and non-standard bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

In one embodiment, the use of non-standard bases according to this disclosure is extendable beyond preparation and use of IAPs for increasing the annealing specificity of an amplification reaction. For example, non-standard bases can be recognized by many enzymes that catalyze reactions associated with nucleic acids. While a polymerase requires a complementary nucleotide to continue polymerizing an extending oligonucleotide chain, other enzymes do not require a complementary nucleotide. If a non-standard base is present in the template and its complementary non-standard base is not present in the reaction mix, a polymerase will typically stall, or misincorporate a base when given a sufficient amount of time, when attempting to extend an elongating primer past the non-standard base. However, other enzymes that catalyze reactions associated with nucleic acids, such as ligases, kinases, nucleases, polymerases, topoisomerases, helicases, and the like, can catalyze reactions involving non-standard bases. Such features of non-standard bases can be taken advantage of, and are within the scope of the present technology.

As mentioned above, the polymerase can in some instances misincorporate a base opposite a non-standard base. In this embodiment, the misincorporation takes place because the reaction mix does not include a complementary non-standard base. Thus, if given sufficient amount of time, the polymerase can in some cases misincorporate a base that is present in the reaction mixture opposite the non-standard base.

III. IAP Kits

One aspect of the present technology discloses a kit containing reagents and instructions for performing amplification reactions with increased annealing specificity. In one embodiment, the kit contains IAPs including a 5'-segment complementary to a nucleic acid template, which is separated from a specific 3'-segment sequence complementary to a template nucleic acid, by an iso-region. In one embodiment, the kit contains an IAP composed of an iso-region with at least two contiguous or non-contiguous non-standard bases. In another embodiment, the kit contains non-standard nucleotide triphosphates, i.e., iso-C and/or iso-G. The kits of the present technology may also include reagents for performing PCR reactions such as buffers, DNA polymerase(s), DNA polymerase cofactors, and deoxyribonucleotide-5'-triphosphates, i.e., dNTPs, or ribonucleotide-5'-triphosphates, i.e., NTPs. In one embodiment, the kits may also include various polynucleotide molecules such as reverse transcriptase and/or antibodies that inhibit DNA polymerase activity.

In one embodiment, the kits contain reagents necessary for performing positive and negative control reactions. In another embodiment, the kits are adapted to contain in separate compartments the constituents as described herein. The kit may also disclose instructions for the diagnosis of genetic and infectious diseases, gender determination, genetic linkage analysis, and additional forensic studies. In another embodiment, reagents employed in the methods of the present technology can be packaged into diagnostic kits. Diagnostic kits may include labeled templates or sequences thereof, IAPs, and conventional primers. In one embodiment the kit includes non-standard bases capable of being incorporated into an elongating oligonucleotide by a polymerase. In another embodiment, the kit contains non-standard bases which are labeled. If the oligonucleotide and non-standard bases are unlabeled, the specific labeling reagents may also be included in the kit. In one embodiment, the kit discloses reagents and instructions for performing or producing any of the methods, steps, procedures or embodiments described herein.

EXAMPLES

The present technology is further illustrated by the following examples, which should not be construed as limiting in any way.

Methods for Amplifying a Target Nucleic Acid Sequence Using IAP Primers

The IAPs disclosed herein are applied to amplify a target nucleic acid. The following experiments are conducted in single-stage PCR amplifications. The IAPs are adapted from conventional or standard primer sets to demonstrate that the IAP system can overcome the main problems arising from these conventional or standard primer sets, such as background and non-specific product amplification. As such, IAP primers were designed to have various melting temperatures (Tm) and contain at least 2 contiguous or non-contiguous iso-bases, with or without interspersed standard bases. The 5' segments contain a variable number of bases to produce an IAP possessing a Tm between about 50° C.-65° C. The 3' segment of the following IAP primers contains between about 4 to 10 bases.

During PCR amplification, an IAP primer set is used to generate and/or detect fragments of a target nucleic acid. Specifically, single-stage PCR amplifications were performed by adding 1 µl of 5' IAP (10 µM) and 1 µl of 3' IAP (10 µM) to a reaction mixture containing, in a final volume of 25 µl, 10 mM of BTP buffer (50 mM KCl, 2.5 mM $MgCl_2$, 0.1 mM of dNTPs, 80 µM of iso-CTP) at pH 9.1, and 1× of TiTaq polymerase (Clontech, Palo Alto, Calif.). The PCR cycling conditions included pre-heating the reaction for 2 minutes at 94° C. followed by 50-70 reaction cycles that included a 5 second (s) denaturation at 95° C., annealing for 20 s at 45° C. or 55° C., and extension for 30 s at 72° C.

As demonstrated by the examples that follow, target nucleotide amplification was indicated, in real time, by a change in fluorescence (denoted as counts in the Tables that follow) due to the production of quenched amplification products or intercalation of SYBR Green into the amplicons. Following amplification, the resulting products were subjected to strand separation, via thermal denaturation, resulting in regeneration of the fluorescent signal. Additionally, the specific temperature at which the melting occurred was used to confirm the identity of the amplification products, i.e., using high resolution melt analysis (see Tables 1-10). Target DNA or RNA was also amplified using standard primers as a control.

Example 1

Detection of Target DNA Using IAPs with Contiguous Iso-Bases

Amplification of a 10,000× LoD Flu A (Flu A) DNA target occurred in the presence of a forward IAP primer with two contiguous iso-G bases and a standard Flu A reverse primer conjugated to FAM (fluorescein). The IAP primer had a 5' segment Tm of 60° C. and varying number of bases, ranging from 4 to 7, at the 3' end (see Table 1). The cycling conditions for the PCR amplification reaction included pre-heating the reaction at 94° C. for 2 minutes followed by 70 reaction cycles including a 5 s denaturation at 95° C., annealing for 20 s at 45° C., and extension for 30 s at 72° C. As shown in Table 1, the decrease in fluorescence (counts) was due to the production of quenched amplicons with each amplification cycle, measured in real-time, and served as an indicator of target DNA amplification. Following amplification, the resulting amplicons were subject to strand separation, via thermal denaturation, resulting in regeneration of fluorescent signal. The specific temperature at which the melting occurred was used to confirm the identity of the amplification products (see Table 1 "Tm").

IAP primer containing two contiguous iso-G bases and an iso-C base conjugated to FAM. The IAP primer had a 5' segment Tm of 55° C. and varying number of bases, ranging from 4 to 7, at the 3' end (see Table 2). The cycling conditions, detection, and amplicon confirmation were performed as outlined above.

TABLE 1

IAP primers with a 60° C. Tm at the 5' end

| Sample ID | Primer ID | Primer Sequences | # of 3' Bases | $C_T$ | $T_m$ |
|---|---|---|---|---|---|
| 1 | FluA-F 4-60 | CAGTGAGCGAGGACTGCYYCGTA (SEQ ID NO: 1) | 4 | 32.5 | 81.2 |
| 2 | FluA-F 4-60 | CAGTGAGCGAGGACTGCYYCGTA (SEQ ID NO: 1) | 4 | 32.6 | 81.0 |
| 3 | FluA-F 5-60 | CCAGTGAGCGAGGACTGYYGCGTA (SEQ ID NO: 2) | 5 | 37.1 | 81.0 |
| 4 | FluA-F 5-60 | CCAGTGAGCGAGGACTGYYGCGTA (SEQ ID NO: 2) | 5 | 37.9 | 81.0 |
| 5 | FluA-F 6-60 | CCCAGTGAGCGAGGACTYYAGCGTA (SEQ ID NO: 3) | 6 | 41.9 | 80.7 |
| 6 | FluA-F 6-60 | CCCAGTGAGCGAGGACTYYAGCGTA (SEQ ID NO: 3) | 6 | 40.0 | 80.8 |
| 7 | FluA-F 7-60 | GCCCAGTGAGCGAGGACYYCAGCGTA (SEQ ID NO: 4) | 7 | 30.2 | 82.2 |
| 8 | FluA-F 7-60 | GCCCAGTGAGCGAGGACYYCAGCGTA (SEQ ID NO: 4) | 7 | 30.1 | 82.2 |
| 9 | FluA-Forward | GCGAGGACTGCAGCGTA (SEQ ID NO: 5) | All standard bases | 27.4 | 78.5 |
| 10 | FluA-Forward | GCGAGGACTGCAGCGTA (SEQ ID NO: 5) | All standard bases | 27.4 | 78.6 |
|  | Reverse Primer | FAM-XAGGGCATTTTGGACAAAGC (SEQ ID NO: 6) | For All Reactions | | |

Note:
X = IsoC, Y = IsoG, FAM = Fluorescein

Amplification of a Flu A DNA target was also performed in the presence of a standard Flu A forward primer and a reverse

TABLE 2

IAP primers with a 55° C. Tm at the 5' end

| Sample ID | Primer ID | Primer Sequences | # of 3' Bases | $C_T$ | $T_m$ |
|---|---|---|---|---|---|
| 1 | FluA-R 3'-5-55C | FAM-XCCATTGAGGGCATTTTGGYYAAAGC (SEQ ID NO: 7) | 5 | 46.1 | 81.0 |
| 2 | FluA-R 3'-5-55C | FAM-XCCATTGAGGGCATTTTGGYYAAAGC (SEQ ID NO: 7) | 5 | 46.0 | 80.9 |
| 3 | FluA-R 3'-6-55C | FAM-XCCCATTGAGGGCATTTTGYYCAAAGC (SEQ ID NO: 8) | 6 | 40.6 | 81.5 |

TABLE 2-continued

IAP primers with a 55° C. Tm at the 5' end

| Sample ID | Primer ID | Primer Sequences | # of 3' Bases | $C_T$ | $T_m$ |
|---|---|---|---|---|---|
| 4 | FluA-R 3'-6-55C | FAM-XCCCATTGAGGGCATTTTGYYCAAAGC (SEQ ID NO: 8) | 6 | 39.6 | 82.0 |
| 5 | FluA-Reverse | FAM-XAGGGCATTTTGGACAAAGC (SEQ ID NO: 6) | Standard FAM labeled | 28.3 | 78.7 |
| 6 | FluA-Reverse | FAM-XAGGGCATTTTGGACAAAGC (SEQ ID NO: 6) | Standard FAM labeled | 27.5 | 78.7 |
|   | Forward Primer | GCGAGGACTGCAGCGTA (SEQ ID NO: 5) | For All Reactions | | |

Note:
X = IsoC, Y = IsoG, FAM = Fluorescein

These results indicate that, in the presence of a standard primer, forward or reverse IAP primers containing contiguous iso-bases are capable of specifically and efficiently amplifying target DNA in real time. These results indicate that IAP primers containing contiguous iso-bases are capable of specifically and efficiently amplifying target DNA in real time, irrespective of whether they are used as the forward primer or as the reverse primer in a PCR reaction.

Example 2

Detection of Target RNA Using IAPs with Contiguous Iso-Bases

Amplification of a Flu A RNA target occurred in the presence of a forward IAP primer with two contiguous iso-G bases and a standard Flu A reverse primer conjugated to FAM. The IAP primer had a 5' segment Tm of 50° C. and varying number of bases, ranging from 4 to 7, at the 3' end (see Table 3). RNA was reverse transcribed using MMLV-RT (Promega, Madison, Wis.) at 50° C. for 15 min prior to amplification. The cycling conditions for the PCR amplification reaction included pre-heating the reaction at 94° C. for 2 minutes followed by 70 reaction cycles including a 5 s denaturation at 95° C., annealing for 20 s at 45° C., and extension for 30 s at 72° C. As shown in Table 3, the decrease in fluorescence (counts) was due to the production of quenched amplicons. Confirmation of amplicon identification was also performed, as described above.

TABLE 3

IAP primers with a 50° C. Tm at the 5' end

| Sample ID | Primer ID | Primer Sequences | # of 3' Bases | $C_T$ | $T_m$ |
|---|---|---|---|---|---|
| 1 | FluA-F 3'-4-50 | CGAGCGAGGACTGCYYCGTA (SEQ ID NO: 9) | 4 | 27.8 | 81.7 |
| 2 | FluA-F 3'-4-50 | CGAGCGAGGACTGCYYCGTA (SEQ ID NO: 9) | 4 | 28.2 | 81.8 |
| 3 | FluA-F 3'-5-50 | CTGAGCGAGGACTGYYGCGTA (SEQ ID NO: 10) | 5 | 35.5 | 81.5 |
| 4 | FluA-F 3'-5-50 | CTGAGCGAGGACTGYYGCGTA (SEQ ID NO: 10) | 5 | 35.6 | 81.4 |
| 5 | FluA-F 3'-6-50 | CGTGAGCGAGGACTYYAGCGTA (SEQ ID NO: 11) | 6 | 37.4 | 80.9 |
| 6 | FluA-F 3'-6-50 | CGTGAGCGAGGACTYYAGCGTA (SEQ ID NO: 11) | 6 | 37.8 | 80.9 |
| 7 | FluA-F 3'-7-50 | CAGTGAGCGAGGACYYCAGCGTA (SEQ ID NO: 12) | 7 | 26.7 | 82.0 |
| 8 | FluA-F 3'-7-50 | CAGTGAGCGAGGACYYCAGCGTA (SEQ ID NO: 12) | 7 | 26.2 | 82.0 |
| 9 | FluA Forward | GCGAGGACTGCAGCGTA (SEQ ID NO: 5) | All standard bases | 23.2 | 78.3 |
| 10 | FluA Forward | GCGAGGACTGCAGCGTA (SEQ ID NO: 5) | All standard bases | 23.4 | 78.3 |

TABLE 3-continued

IAP primers with a 50° C. Tm at the 5' end

| Sample ID | Primer ID | Primer Sequences | # of 3' Bases | $C_T$ | $T_m$ |
|---|---|---|---|---|---|
| | Reverse Primer | FAM-XAGGGCATTTTGGACAAAGC (SEQ ID NO: 6) | FAM labeled primer - For All Reactions | | |

Note:
X = IsoC, Y = IsoG, FAM = Fluorescein

Amplification of a Flu A RNA target was also performed in the presence of a standard Flu A forward primer and a reverse IAP primer containing two contiguous iso-G bases and an iso-C base conjugated to FAM. The IAP primer had a 5' segment Tm of 55° C. and varying number of bases, ranging from 5 to 7, at the 3' end (see Table 4). The cycling conditions, detection, and amplicon confirmation were performed as outlined above.

TABLE 4

IAP primers with a 55° C. Tm at the 5' end

| Sample ID | Primer ID | Primer Sequences | # of 3' Bases | $C_T$ | $T_m$ |
|---|---|---|---|---|---|
| 1 | FluA-R 3'-5-55CFAM- | XCCATTGAGGGCATTTTGGYYAAAGC (SEQ ID NO: 7) | 5 | 39.4 | 80.7 |
| 2 | FluA-R 3'-5-55CFAM- | XCCATTGAGGGCATTTTGGYYAAAGC (SEQ ID NO: 7) | 5 | 38.9 | 80.6 |
| 3 | FluA-R 3'-5-55CFAM- | XCCATTGAGGGCATTTTGGYYAAAGC (SEQ ID NO: 7) | 5 | 39.5 | 80.6 |
| 4 | FluA-R 3'-6-55CFAM- | XCCCATTGAGGGCATTTTGYYCAAAGC (SEQ ID NO: 8) | 6 | 33.4 | 81.3 |
| 5 | FluA-R 3'-6-55CFAM- | XCCCATTGAGGGCATTTTGYYCAAAGC (SEQ ID NO: 8) | 6 | 33.9 | 81.3 |
| 6 | FluA-R 3'-6-55CFAM- | XCCCATTGAGGGCATTTTGYYCAAAGC (SEQ ID NO: 8) | 6 | 33.5 | 81.2 |
| 7 | FluA Reverse | FAM-XAGGGCATTTTGGACAAAGC (SEQ ID NO: 6) | Standard FAM labeled | 22.9 | 78.4 |
| 8 | FluA Reverse | FAM-XAGGGCATTTTGGACAAAGC (SEQ ID NO: 6) | Standard FAM labeled | 23.1 | 78.4 |
| 9 | FluA Reverse | FAM-XAGGGCATTTTGGACAAAGC (SEQ ID NO: 6) | Standard FAM labeled | 22.7 | 78.3 |
| | Forward Primer | GCGAGGACTGCAGCGTA (SEQ ID NO: 5) | All standard bases - For All Reactions | | |

Note:
X = IsoC, Y = IsoG, FAM = Fluorescein

These results indicate that, in the presence of a standard primer, forward or reverse IAP primers containing contiguous iso-bases are capable of specifically and efficiently amplifying target RNA in real time. These results indicate that IAP primers containing contiguous iso-bases are capable of specifically and efficiently amplifying target RNA in real time, irrespective of whether they are used as the forward primer or as the reverse primer in a PCR reaction. In addition, these results indicate that the IAP primer (forward primer) is capable of priming the RNA for the reverse transcriptase reaction.

Example 3

SYBR Green Detection of Target DNA Using IAPs

Amplification of a Flu A DNA target occurred in the presence of a forward IAP primer with two contiguous iso-G bases and a standard reverse primer. The IAP primers had a 5' segment Tm of 55° C. and varying number of bases, ranging from 4 to 7, at the 3' end (see Table 5). The PCR amplification reactions employed the double-stranded (ds) DNA intercalating dye SYBR Green and cycling conditions that included pre-heating the reaction at 94° C. for 2 minutes followed by 70 reaction cycles including a 5 s denaturation at 95° C., annealing for 20 s at 55° C., and extension for 30 s at 72° C. As shown in Table 5, changes in fluorescence (counts) were due to SYBR Green intercalation into the ds amplicon, as measured in real-time, and served as an indicator of target DNA amplification. Confirmation of amplicon identification was also performed, as described above.

TABLE 5

IAP primers with a 55° C. Tm at the 5' end and SYBR

| Sample ID | Primer ID | Primer Sequences | # of 3' Bases | $C_T$ | $T_m$ |
|---|---|---|---|---|---|
| 1 | FluA-F 3'-4-55 | CTGAGCGAGGACTGCYYCGTA (SEQ ID NO: 13) | 4 | 41.5 | 81.4 |
| 2 | FluA-F 3'-4-55 | CTGAGCGAGGACTGCYYCGTA (SEQ ID NO: 13) | 4 | 41.8 | 81.4 |
| 3 | FluA-F 3'-5-55 | CAGTGAGCGAGGACTGYYGCGTA (SEQ ID NO: 14) | 5 | 41.2 | 81.4 |
| 4 | FluA-F 3'-5-55 | CAGTGAGCGAGGACTGYYGCGTA (SEQ ID NO: 14) | 5 | 40.7 | 81.6 |
| 5 | FluA-F 3'-6-55 | CCAGTGAGCGAGGACTYYAGCGTA (SEQ ID NO: 15) | 6 | 47.4 | 80.8 |
| 6 | FluA-F 3'-6-55 | CCAGTGAGCGAGGACTYYAGCGTA (SEQ ID NO: 15) | 6 | 45.5 | 80.5 |
| 7 | FluA-F 3'-7-55 | CCCAGTGAGCGAGGACYYCAGCGTA (SEQ ID NO: 16) | 7 | 28.6 | 81.6 |
| 8 | FluA-F 3'-7-55 | CCCAGTGAGCGAGGACYYCAGCGTA (SEQ ID NO: 16) | 7 | 29.0 | 81.6 |
| 9 | FluA Forward | GCGAGGACTGCAGCGTA (SEQ ID NO: 5) | All Standard bases | 23.9 | 78.5 |
|  | Reverse Primer | XAGGGCATTTTGGACAAAGC (SEQ ID NO: 6) | For All Reactions |  |  |

Note:
X = IsoC, Y = IsoG

Example 4

SYBR Green Detection of DNA Using IAPs with Non-Contiguous Iso-Bases

Amplification of a Flu A DNA target occurred in the presence of a reverse IAP primer with two non-contiguous iso-G bases, separated by one natural base, and a standard forward primer. The IAP primers had a 5' segment Tm of 60° C. and 4 bases at the 3' end (see Table 6). The PCR amplification reactions used the ds DNA intercalating dye SYBR Green and cycling conditions that included pre-heating the reaction at 94° C. for 2 minutes followed by 70 reaction cycles including a 5 s denaturation at 95° C., annealing for 20 s at 55° C., and extension for 30 s at 72° C. As shown in Table 6, changes in fluorescence (counts) were due to SYBR Green intercalation into the ds amplicon, as measured in real-time, and served as an indicator of target DNA amplification. Confirmation of amplicon identification was also performed, as described above.

TABLE 6

IAP primers with a 60° C. Tm at the 5' end and SYBR

| Sample ID | Primer ID | Primer Sequences | # of 3' Bases | $C_T$ | $T_m$ |
|---|---|---|---|---|---|
| 1 | FluA-R-3'-4-GYTYG | GGATCCCCATTCCCATTGYTYGCAT (SEQ ID NO: 17) | 4 | 39.6 | 81.9 |
| 2 | FluA-R-3'-4-GYTYG | GGATCCCCATTCCCATTGYTYGCAT (SEQ ID NO: 17) | 4 | 40.5 | 81.9 |
| 3 | FluA-R-3'-4-GYTYG | GGATCCCCATTCCCATTGYTYGCAT (SEQ ID NO: 17) | 4 | 40.1 | 81.8 |
| 4 | FluA-R-3'-4-GYTYG | GGATCCCCATTCCCATTGYTYGCAT (SEQ ID NO: 17) | 4 | 38.1 | 81.8 |

TABLE 6-continued

IAP primers with a 60° C. Tm at the 5' end and SYBR

| Sample ID | Primer ID | Primer Sequences | # of 3' Bases | $C_T$ | $T_m$ |
|---|---|---|---|---|---|
| 5 | FluA Reverse | XAGGGCATTTTGGACAAAGC (SEQ ID NO: 6) | Standard | 24.1 | 78.1 |
| 6 | FluA Reverse | XAGGGCATTTTGGACAAAGC (SEQ ID NO: 6) | Standard | 24.7 | 78.3 |
|  | Forward Primer | GCGAGGACTGCAGCGTA (SEQ ID NO: 5) | For All Reactions | | |

Note:
X = IsoC, Y = IsoG

These results indicate that, in the presence of a standard primer, IAP primers containing non-contiguous iso-bases are capable of specifically and efficiently amplifying target DNA in real time. These results indicate that intercalating dyes can be used as suitable detection agents in amplification reactions and for high resolution melt analyses. Specifically, the results indicate that intercalating dyes such as SYBR Green is a suitable detection agent for use in the IAP amplification reactions.

Example 5

SYBR Green Detection of DNA Using Forward and Reverse IAPs

Amplification of a Flu A DNA target occurred in the presence of forward and reverse IAP primers each with two contiguous iso-G bases. The IAP primers had 5' segment Tm's of 50° C., 55° C., and 60° C., and varying number of bases, ranging from 4 to 7, at the 3' end (see Tables 7-9, respectively). The PCR amplification reactions used the ds DNA intercalating dye SYBR Green and cycling conditions that included pre-heating the reaction at 94° C. for 2 minutes followed by 70 reaction cycles including a 5 s denaturation at 95° C., annealing for 20 s at 55° C., and extension for 30 s at 72° C. As shown in Tables 7-9, changes in fluorescence (counts) were due to SYBR Green intercalation into the ds amplicon, as measured in real-time, and served as an indicator of target DNA amplification. Confirmation of amplicon identification was also performed, as described above.

TABLE 7

IAP primers with a 50° C. Tm at the 5' end and SYBR

| Specimen ID | Primer ID | Primer Sequences | # of 3' Bases | $C_T$ | $T_m$ |
|---|---|---|---|---|---|
| 1 | FluA-F-3'-4-50 | CGAGCGAGGACTGCYYCGTA (SEQ ID NO: 9) | 4 | 42.4 | 84.7 |
| 2 | FluA-F-3'-4-50 | CGAGCGAGGACTGCYYCGTA (SEQ ID NO: 9) | 4 | 43.4 | 84.7 |
| 3 | FluA-F-3'-5-50 | CTGAGCGAGGACTGYYGCGTA (SEQ ID NO: 10) | 5 | 41.9 | 84.5 |
| 4 | FluA-F-3'-5-50 | CTGAGCGAGGACTGYYGCGTA (SEQ ID NO: 10) | 5 | 40.3 | 84.5 |
| 5 | FluA-F-3'-6-50 | CGTGAGCGAGGACTYYAGCGTA (SEQ ID NO: 11) | 6 | 45.6 | 84.0 |
| 6 | FluA-F-3'-6-50 | CGTGAGCGAGGACTYYAGCGTA (SEQ ID NO: 11) | 6 | 42.9 | 84.1 |
| 7 | FluA-F-3'-7-50 | CAGTGAGCGAGGACYYCAGCGTA (SEQ ID NO: 12) | 7 | 31.9 | 85.0 |
| 8 | FluA-F-3'-7-50 | CAGTGAGCGAGGACYYCAGCGTA (SEQ ID NO: 12) | 7 | 32.3 | 85.0 |
| 9 | FluA Forward | GCGAGGACTGCAGCGTA (SEQ ID NO: 5) | Standard | 30.0 | 82.2 |
|  | Flu A Reverse | XAGGGCATTTTGGACAAAGC (SEQ ID NO: 6) | | | |
| 10 | FluA Forward | GCGAGGACTGCAGCGTA (SEQ ID NO: 5) | Standard | 29.7 | 82.2 |

TABLE 7-continued

IAP primers with a 50° C. Tm at the 5' end and SYBR

| Specimen ID | Primer ID | Primer Sequences | # of 3' Bases | $C_T$ | $T_m$ |
|---|---|---|---|---|---|
| | Flu A Reverse | XAGGGCATTTTGGACAAAGC (SEQ ID NO: 6) | | | |
| | FluA-R-3'-4-CT Reverse Primer | CCCATTCCCATTGAGGGCYYTTTG (SEQ ID NO: 18) | For All Reactions with IAP primer | | |

Note:
X = IsoC, Y = IsoG

TABLE 8

IAP primers with a 55° C. Tm at the 5' end and SYBR

| Specimen ID | Primer ID | Primer Sequences | # of 3' Bases | $C_T$ | $T_m$ |
|---|---|---|---|---|---|
| 1 | FluA-F-3'-4-55 | CTGAGCGAGGACTGCYYCGTA (SEQ ID NO: 13) | 4 | 46.5 | 84.5 |
| 2 | FluA-F-3'-4-55 | CTGAGCGAGGACTGCYYCGTA (SEQ ID NO: 13) | 4 | 47.2 | 84.3 |
| 3 | FluA-F-3'-5-55 | CAGTGAGCGAGGACTGYYGCGTA (SEQ ID NO: 14) | 5 | 42.8 | 84.2 |
| 4 | FluA-F-3'-5-55 | CAGTGAGCGAGGACTGYYGCGTA (SEQ ID NO: 14) | 5 | 41.3 | 84.1 |
| 5 | FluA-F-3'-6-55 | CCAGTGAGCGAGGACTYYAGCGTA (SEQ ID NO: 15) | 6 | 45.9 | 83.5 |
| 6 | FluA-F-3'-6-55 | CCAGTGAGCGAGGACTYYAGCGTA (SEQ ID NO: 15) | 6 | 42.6 | 83.3 |
| 7 | FluA-F-3'-7-55 | CCCAGTGAGCGAGGACYYCAGCGTA (SEQ ID NO: 16) | 7 | 33.2 | 84.1 |
| 8 | FluA-F-3'-7-55 | CCCAGTGAGCGAGGACYYCAGCGTA (SEQ ID NO: 16) | 7 | 33.1 | 84.1 |
| 9 | FluA Forward | GCGAGGACTGCAGCGTA (SEQ ID NO: 5) | Standard | 30.0 | 82.2 |
| | FluA Reverse | XAGGGCATTTTGGACAAAGC (SEQ ID NO: 6) | | | |
| 10 | FluA Forward | GCGAGGACTGCAGCGTA (SEQ ID NO: 5) | Standard | 29.7 | 82.2 |
| | FluA Reverse | XAGGGCATTTTGGACAAAGC (SEQ ID NO: 6) | | | |
| | FluA-R-3'-4-CT Reverse Primer | CCCATTCCCATTGAGGGCYYTTTG (SEQ ID NO: 18) | For All Reactions with IAP primer | | |

Note:
X = IsoC, Y = IsoG

TABLE 9

IAP primers with a 60° C. Tm at the 5' end and SYBR

| Specimen ID | Primer ID | Primer Sequences | # of 3' Bases | $C_T$ | $T_m$ |
|---|---|---|---|---|---|
| 1 | FluA-F-3'-4-60 | CCAGTGAGCGAGGACTGCYYCGTA (SEQ ID NO: 1) | 4 | 58.6 | |

TABLE 9-continued

IAP primers with a 60° C. Tm at the 5' end and SYBR

| Specimen ID | Primer ID | Primer Sequences | # of 3' Bases | $C_T$ | $T_m$ |
|---|---|---|---|---|---|
| 2 | FluA-F-3'-4-60 | CCAGTGAGCGAGGACTGCYYCGTA (SEQ ID NO: 1) | 4 | 48.7 | 83.6 |
| 3 | FluA-F-3'-5-60 | CCCAGTGAGCGAGGACTGYYGCGTA (SEQ ID NO: 2) | 5 | 43.1 | 83.7 |
| 4 | FluA-F-3'-5-60 | CCCAGTGAGCGAGGACTGYYGCGTA (SEQ ID NO: 2) | 5 | 45.0 | 83.7 |
| 5 | FluA-F-3'-6-60 | CCCCAGTGAGCGAGGACTYYAGCGTA (SEQ ID NO: 3) | 6 | 47.1 | 83.1 |
| 6 | FluA-F-3'-6-60 | CCCCAGTGAGCGAGGACTYYAGCGTA (SEQ ID NO: 3) | 6 | 47.7 | 83.1 |
| 7 | FluA-F-3'-7-60 | CGCCCAGTGAGCGAGGACYYCAGCGTA (SEQ ID NO: 4) | 7 | 34.8 | 84.3 |
| 8 | FluA-F-3'-7-60 | CGCCCAGTGAGCGAGGACYYCAGCGTA (SEQ ID NO: 4) | 7 | 35.0 | 84.3 |
| 9 | FluA Forward | GCGAGGACTGCAGCGTA (SEQ ID NO: 5) | Standard | 30.0 | 82.2 |
|   | FluA Reverse | XAGGGCATTTTGGACAAAGC (SEQ ID NO: 6) |  |  |  |
| 10 | FluA Forward | GCGAGGACTGCAGCGTA (SEQ ID NO: 5) | Standard | 29.7 | 82.2 |
|   | FluA Reverse | XAGGGCATTTTGGACAAAGC (SEQ ID NO: 6) |  |  |  |
|   | FluA-R-3'-4-CT-Reverse Primer | CCCATTCCCATTGAGGGCYYTTTG (SEQ ID NO: 18) | For All Reactions with IAP primer |  |  |

Note:
X = IsoC, Y = IsoG

Example 6

IAPs Decrease Non-specific Interactions

Amplification of a Flu A DNA target was performed in the presence of forward and reverse IAP primers each with two contiguous iso-G bases and compared to a control reaction using standard primers. The IAP primers had a 5' segment Tm of 50° C. and 5 bases at the 3' end. The PCR amplification reactions used the ds DNA intercalating dye SYBR Green and cycling conditions that included pre-heating the reaction at 94° C. for 2 minutes followed by 50 reaction cycles including a 5 s denaturation at 95° C., annealing for 20 s at 55° C., and extension for 30 s at 72° C. As shown in Table 10, changes in fluorescence (counts) were due to SYBR Green intercalation into the ds amplicon, as measured in real-time, and served as an indicator of target DNA amplification. Confirmation of amplicon identification was also performed, as described above. It is noted that the amplification performed in the presence of the IAP primers (see Table 10) had fewer non-specific interactions compared to the control reaction using standard Flu A forward and reverse primers (see Table 10).

TABLE 10

SYBR Green-based PCR reactions with IAP primers compared to reactions using standard primers

| Set | Primer ID | Primer Sequences | FluA Target/Avg. Ct | # of Dimers in NTC Rxn | Avg. Dimer Ct |
|---|---|---|---|---|---|
| A | FluA-F-3'-5-50 | CTGAGCGAGGACTGYYGCGTA (SEQ ID NO: 10) | 36.3 | 1 | 42.5 |
|   | FluA-R-3'-4-CT | CCCATTCCCATTGAGGGCYYTTTG (SEQ ID NO: 18) |  |  |  |

TABLE 10-continued

SYBR Green-based PCR reactions with IAP primers compared
to reactions using standard primers

| Set | Primer ID | Primer Sequences | FluA Target/Avg. Ct | # of Dimers in NTC Rxn | Avg. Dimer Ct |
|---|---|---|---|---|---|
| B | Flu A For | GCGAGGACTGCAGCGTA (SEQ ID NO: 5) | 24 | 6 | 31.9 |
|   | Flu A Rev | XAGGGCATTTTGGACAAAGC (SEQ ID NO: 6) | | | |

The foregoing examples illustrate that IAPs are capable of detecting target nucleotide sequences that are essentially free of non-specific background products, thus ameliorating problems such as non-specificity, which arise when using conventional primers. It is also understood that the IAP assays allow for the generation specific products regardless of the design of gene-specific primers.

\* \* \* \*

The present disclosure is not to be limited in terms of the particular embodiments described in this application, which are intended as single illustrations of individual aspects of. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 "X" refers to groups having 1, 2, or 3 "X's". Similarly, a group having 1-5 "X's" refers to groups having 1, 2, 3, 4, or 5 "X's", and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for amplifying a template nucleic acid in a two-stage reaction comprising:
   (a) performing a first-stage amplification of a template sequence at a first annealing temperature to form a first amplification product, the first-stage amplification comprising at least two cycles of denaturing the template sequence, annealing at least one primer, and extending the at least one primer, wherein the at least one primer comprises:
      (i) a 3'-segment complementary to a first region of the template sequence;
      (ii) a 5'-segment complementary to a second region of the template sequence; and
      (iii) an iso-region between the 3'-segment and the 5'-segment, wherein the iso-region comprises at least two contiguous or non-contiguous non-standard bases independently selected from the group consisting of: K, X, H, J, M, N, iso-C and iso-G; and
   (b) performing a second-stage amplification of the first amplification product at a second annealing temperature that is higher than the first annealing temperature comprising at least one cycle of denaturing the amplification product generated from step (a), annealing the at least one primer, and extending the at least one primer.

2. The method according to claim 1, wherein the template nucleic acid is a cDNA formed by (a) hybridizing an oligonucleotide dT primer or an anchored oligonucleotide dT primer to a poly-A tail region of a target mRNA, or hybridizing random hexamer, heptamer, and/or octomer oligonucleotides to a target mRNA; and (b) reverse transcribing the target mRNA to produce the cDNA.

3. The method according to claim 1, wherein the two-stage amplification procedure is applied to a method selected from the group consisting of: PCR; multiplex DNA amplification; identification of differentially expressed genes; 3'-Rapid Amplification of cDNA Ends; primer extension reactions; 5'-Rapid Amplification of cDNA Ends; amplifying full-length cDNA; amplifying 5'-enriched cDNA; DNA fingerprinting; RNA fingerprinting; identification of conserved homology segments in multigene families; identification of nucleotide sequence variations; pre-miRNA amplification; rRNA amplification; high resolution melt analysis following PCR; and mutagenesis.

4. The method of claim 1, wherein the non-standard bases are contiguous.

5. The method of claim 1, wherein the non-standard bases are non-contiguous.

6. The method of claim 1, wherein the iso-region consists of 2, 3, or 4 bases.

7. The method of claim 6, wherein all of the bases in the iso-region are non-standard bases.

8. The method of claim 1, wherein the 3'-segment is 4 to 7 bases in length.

9. The method of claim 1, wherein the 5'-segment is 6 to 60 bases in length.

10. The method of claim 1, wherein the 3'-segment is 4 to 7 bases in length, the 5'-segment is 6 to 60 bases in length, and the iso-region is 2 to 4 bases in length.

11. The method of claim 1, wherein the 5'-segment further comprises a label.

12. The method of claim 1, wherein the non-standard bases are independently selected from the group consisting of iso-C and iso-G.

\* \* \* \* \*

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (18)..(19)
<223> OTHER INFORMATION: n represents deoxy-iso-guanine (d-isoG)

<400> SEQUENCE: 1
cagtgagcga ggactgcnnc gta                                              23

<210> SEQ ID NO 2
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (18)..(19)
<223> OTHER INFORMATION: n represents deoxy-iso-guanine (d-isoG)

<400> SEQUENCE: 2
ccagtgagcg aggactgnng cgta                                             24

<210> SEQ ID NO 3
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (18)..(19)
<223> OTHER INFORMATION: n represents deoxy-iso-guanine (d-isoG)

<400> SEQUENCE: 3
cccagtgagc gaggactnna gcgta                                            25

<210> SEQ ID NO 4
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (18)..(19)
<223> OTHER INFORMATION: n represents deoxy-iso-guanine (d-isoG)

<400> SEQUENCE: 4
gcccagtgag cgaggacnnc agcgta                                           26

<210> SEQ ID NO 5
<211> LENGTH: 17
<212> TYPE: DNA
<213> ORGANISM: Artificial Sequence
<220> FEATURE:
<223> OTHER INFORMATION: Synthetic Primer

<400> SEQUENCE: 5
gcgaggactg cagcgta                                                     17

-continued

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (1)..(1)
<223> OTHER INFORMATION: n represents deoxy-iso-cytosine (d-isoC)

<400> SEQUENCE: 6
nagggcattt tggacaaagc                                              20

<210> SEQ ID NO 7
<211> LENGTH: 26
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (1)..(1)
<223> OTHER INFORMATION: n represents deoxy-iso-cytosine (d-isoC)
<220> FEATURE:
<221> NAME/KEY: modified_base
<222> LOCATION: (20)..(21)
<223> OTHER INFORMATION: n represents deoxy-iso-guanine (d-isoG)

<400> SEQUENCE: 7
nccattgagg gcattttggn naaagc                                       26

<210> SEQ ID NO 8
<211> LENGTH: 27
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (1)..(1)
<223> OTHER INFORMATION: n represents deoxy-iso-cytosine (d-isoC)
<220> FEATURE:
<221> NAME/KEY: modified_base
<222> LOCATION: (20)..(21)
<223> OTHER INFORMATION: n represents deoxy-iso-guanine (d-isoG)

<400> SEQUENCE: 8
ncccattgag ggcattttgn ncaaagc                                      27

<210> SEQ ID NO 9
<211> LENGTH: 19
<212> TYPE: DNA
<213> ORGANISM: Artificial Sequence
<220> FEATURE:
<223> OTHER INFORMATION: Synthetic Primer
<220> FEATURE:
<221> NAME/KEY: modified_Base
<222> LOCATION: (14)..(15)
<223> OTHER INFORMATION: n represents deoxy-iso-guanine (d-isoG)

<400> SEQUENCE: 9
gagcgaggac tgcnncgta                                               19

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer
<220> FEATURE:
```

```
<221> NAME/KEY: modified_Base
<222> LOCATION: (14)..(15)
<223> OTHER INFORMATION: n represents deoxy-iso-guanine (d-isoG)

<400> SEQUENCE: 10
tgagcgagga ctgnngcgta                                               20

<210> SEQ ID NO 11
<211> LENGTH: 21
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (14)..(15)
<223> OTHER INFORMATION: n represents deoxy-iso-guanine (d-isoG)

<400> SEQUENCE: 11
gtgagcgagg actnnagcgt a                                             21

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (14)..(15)
<223> OTHER INFORMATION: n represents deoxy-iso-guanine (d-isoG)

<400> SEQUENCE: 12
agtgagcgag gacnncagcg ta                                            22

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (15)..(16)
<223> OTHER INFORMATION: n represents deoxy-iso-guanine (d-isoG)

<400> SEQUENCE: 13
tgagcgagga ctgcnncgta                                               20

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (16)..(17)
<223> OTHER INFORMATION: n represents deoxy-iso-guanine (d-isoG)

<400> SEQUENCE: 14
agtgagcgag gactgnngcg ta                                            22

<210> SEQ ID NO 15
<211> LENGTH: 23
<212> TYPE: DNA
<213> ORGANISM: Artificial Sequence
<220> FEATURE:
<223> OTHER INFORMATION: Synthetic Primer
<220> FEATURE:
```

-continued

```
<221> NAME/KEY: modified_base
<222> LOCATION: (16)..(17)
<223> OTHER INFORMATION: n represents deoxy-iso-guanine (d-isoG)

<400> SEQUENCE: 15
cagtgagcga ggactnnagc gta                                             23

<210> SEQ ID NO 16
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (16)..(17)
<223> OTHER INFORMATION: n represents deoxy-iso-guanine (d-isoG)

<400> SEQUENCE: 16
ccagtgagcg aggacnncag cgta                                            24

<210> SEQ ID NO 17
<211> LENGTH: 25
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (19)..(19)
<223> OTHER INFORMATION: n represents deoxy-iso-guanine (d-isoG)
<220> FEATURE:
<221> NAME/KEY: modified_base
<222> LOCATION: (21)..(21)
<223> OTHER INFORMATION: n represents deoxy-iso-guanine (d-isoG)

<400> SEQUENCE: 17
ggatccccat tcccattgnt ngcat                                           25

<210> SEQ ID NO 18
<211> LENGTH: 24
<212> TYPE: DNA
<213> ORGANISM: Artificial Sequence
<220> FEATURE:
<223> OTHER INFORMATION: Synthetic Primer
<220> FEATURE:
<221> NAME/KEY: modified_base
<222> LOCATION: (19)..(20)
<223> OTHER INFORMATION: n represents deoxy-iso-guanine (d-isoG)

<400> SEQUENCE: 18
cccattccca ttgagggcnn tttg                                            24
```